(12) United States Patent
Kimoto

(10) Patent No.: US 8,300,092 B2
(45) Date of Patent: Oct. 30, 2012

(54) IN-VIVO IMAGE ACQUIRING APPARATUS, IN-VIVO IMAGE RECEIVING APPARATUS, IN-VIVO IMAGE DISPLAYING APPARATUS, AND NOISE ELIMINATING METHOD

(75) Inventor: Seiichiro Kimoto, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 901 days.

(21) Appl. No.: 12/398,505

(22) Filed: Mar. 5, 2009

(65) Prior Publication Data

US 2009/0225158 A1 Sep. 10, 2009

(30) Foreign Application Priority Data

Mar. 5, 2008 (JP) ................................. 2008-055454

(51) Int. Cl.
*A61B 1/06* (2006.01)
*A61B 1/04* (2006.01)
*H04N 13/02* (2006.01)
*G06K 9/38* (2006.01)

(52) U.S. Cl. ............................. 348/68; 348/77; 382/272

(58) Field of Classification Search .................... 348/68, 348/77; 382/272
See application file for complete search history.

(56) References Cited

U.S. PATENT DOCUMENTS

| | | | |
|---|---|---|---|
| 6,995,346 B2 | 2/2006 | Johanneson et al. | |
| 7,465,271 B2 * | 12/2008 | Kanazawa | 600/179 |
| 7,822,248 B2 * | 10/2010 | Ikemoto | 382/128 |
| 7,889,228 B2 * | 2/2011 | Ishihara et al. | 348/65 |
| 2003/0001951 A1 | 1/2003 | Tsujita et al. | |
| 2006/0020214 A1 | 1/2006 | Mori et al. | |
| 2006/0287580 A1 * | 12/2006 | Jo et al. | 600/160 |
| 2007/0002134 A1 * | 1/2007 | Ishihara et al. | 348/65 |
| 2007/0195164 A1 * | 8/2007 | Fukuyama | 348/65 |
| 2007/0269088 A1 * | 11/2007 | Ikemoto | 382/128 |
| 2008/0045792 A1 * | 2/2008 | Shimizu et al. | 600/118 |

(Continued)

FOREIGN PATENT DOCUMENTS

| | | |
|---|---|---|
| JP | 2003-537 A | 1/2003 |
| JP | 2005-211231 A | 8/2005 |
| JP | 2006-020778 | 1/2006 |

(Continued)

OTHER PUBLICATIONS

Japanese Office Action dated Aug. 21, 2012 from corresponding Japanese Patent Application No. JP 2008055454 together with an English language translation.

*Primary Examiner* — George C Neurauter
(74) *Attorney, Agent, or Firm* — Scully, Scott, Murphy & Presser, P.C.

(57) ABSTRACT

An in-vivo image acquiring apparatus includes an operation control unit which controls a black image acquiring operation, in which the operation control unit controls an imaging unit and an illuminating unit in such a manner the imaging unit conducts an image acquiring operation in a state the illuminating unit does not conduct an illuminating operation. The in-vivo image acquiring apparatus also includes an average calculating unit which calculates the average value of pixel value in a predetermined determining area, and a black image determining unit, which determines whether the image information acquired by the image acquiring operation is the black image by comparing the average value with a predetermined threshold value. The image information determined as the black image by the black image determining unit is transmitted, as the black image information, to an external apparatus by radio.

13 Claims, 14 Drawing Sheets

U.S. PATENT DOCUMENTS

| | | | |
|---|---|---|---|
| 2008/0074491 A1* | 3/2008 | Matsui | 348/65 |
| 2008/0100698 A1* | 5/2008 | Mori et al. | 348/65 |
| 2008/0292150 A1* | 11/2008 | Hirakawa | 382/128 |
| 2009/0167908 A1* | 7/2009 | Mori et al. | 348/251 |
| 2010/0259650 A1* | 10/2010 | Sasaki | 348/241 |

FOREIGN PATENT DOCUMENTS

| | | |
|---|---|---|
| JP | 2006-334076 A | 12/2006 |
| JP | 2007-241172 A | 9/2007 |
| WO | WO 02/080376 A2 | 10/2002 |

* cited by examiner

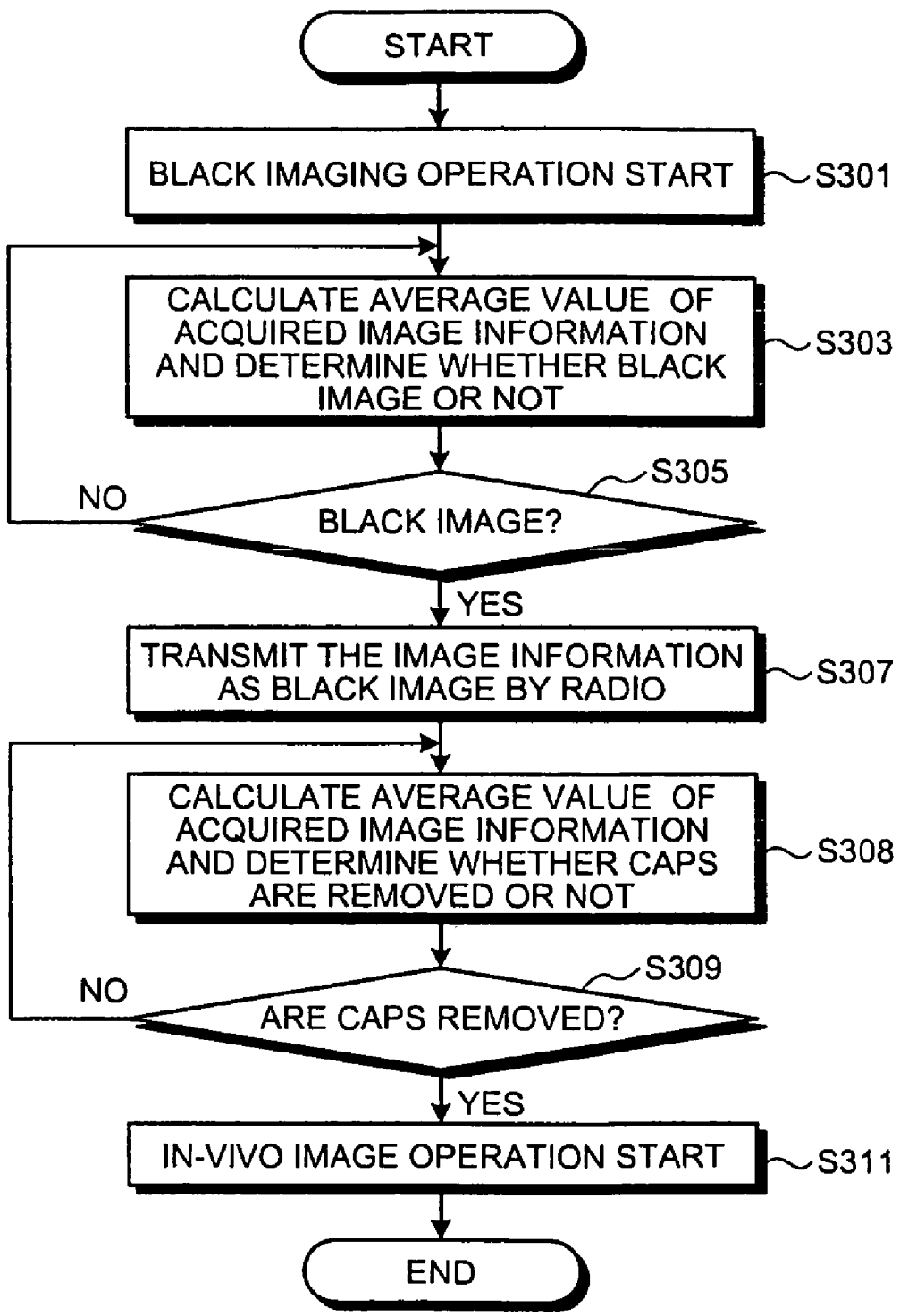

IN-VIVO IMAGE ACQUIRING APPARATUS, IN-VIVO IMAGE RECEIVING APPARATUS, IN-VIVO IMAGE DISPLAYING APPARATUS, AND NOISE ELIMINATING METHOD

CROSS-REFERENCE TO RELATED APPLICATIONS

This application is based upon and claims the benefit of priority from Japanese Patent Application No. 2008-055454, filed on Mar. 5, 2008, the entire contents of which are incorporated herein by reference.

BACKGROUND OF THE INVENTION

1. Field of the Invention

The present invention relates to an in-vivo image acquiring apparatus which is taken into the body of a subject (patient) and acquires in-vivo image information, an in-vivo image receiving apparatus which receives the image information acquired with the in-vivo image acquiring apparatus, an in-vivo image displaying apparatus which displays the image information acquired with the in-vivo image acquiring apparatus, and a noise eliminating method that eliminates fixed pattern noises in the in-vivo image information of the subject.

2. Description of the Related Art

In recent years, in the field of endoscope, a swallow-type capsule endoscope has been proposed. Such capsule endoscope is provided with, in a capsule-shaped case, an imaging unit which acquires in-vivo image information, an illuminating unit which illuminates the imaging regions of which images are taken with the imaging unit, and a transmitting unit which transmits the image information acquired with the imaging unit by radio. The capsule endoscope is swallowed from the mouth of the patient who is the subject and taken into the body of the subject. The capsule endoscope travels inside the body cavity in accordance with its peristaltic motion, takes images inside the body cavity sequentially, and transmits the acquired image information to the outside the body by radio until the endoscope is naturally excreted from the body.

Image sensors including CMOS and CCD are used for taking in-vivo images. Such image sensors generate fixed pattern noises due to fluctuation of output characteristics among each of the pixels and the like. Especially, CMOS image sensor is more likely to generate the fixed pattern noises than CCD does. For a process to eliminate the fixed pattern noises, for a digital camera and the like which are provided with a shutter mechanism, the following process is known. Specifically, as a first step, a black image that includes the fixed pattern noises is acquired by conducting exposure in a state the shutter is closed; then as a second step, the fixed pattern noises are subtracted from the image of the photographic subject which was actually taken. Meanwhile, in the case of the capsule endoscope, as the shutter mechanism is not provided with, the following structure is known, in which the fixed pattern noises are detected by acquiring the black image with the imaging unit in a non-illuminating state by the illuminating unit. (Japanese patent Application Laid-Open No. 2006-20778).

SUMMARY OF THE INVENTION

An in-vivo image acquiring apparatus according to an aspect of the present invention is to be taken into a body of a subject, and includes an imaging unit that acquires in-vivo image information; an illuminating unit that illuminates imaging regions of which images are taken by the imaging unit; a radio transmitting unit that transmits the image information acquired by the imaging unit to an external apparatus by radio; an operation control unit that controls operations of the imaging unit and the illuminating unit so as to control a black image acquiring operation in which the imaging unit conducts an imaging operation with the illuminating unit not conducting an illuminating operation; an average value calculating unit that calculates an average value of pixel values of a predetermined determining area among the image information acquired by the black image acquiring operation; and a black image determining unit that determines whether the image information acquired by the black image acquiring operation indicates a black image by comparing the average value calculated by the average value calculating unit with a predetermined threshold value. The radio transmitting unit transmits to the external apparatus by radio the image information which is determined by the black image determining unit as the black image, as black image information.

An in-vivo image acquiring apparatus according to another aspect of the present invention is to be taken into a body of a subject, and includes an imaging unit that acquires in-vivo image information; an illuminating unit that illuminates imaging regions of which images are taken by the imaging unit; a radio transmitting unit that transmits the image information acquired by the imaging unit to an external apparatus by radio; an operation control unit that controls operations of the imaging unit and the illuminating unit so as to control a black image acquiring operation in which the imaging unit conducts an imaging operation with the illuminating unit not conducting an illuminating operation; a peak detector that detects a peak value of pixel values of pixels that constitute a predetermined determining area among the image information acquired by the black image acquiring operation; and a black image determining unit that determines whether the image information acquired by the black image acquiring operation indicates a black image by comparing the peak value detected by the peak detector with a predetermined threshold value. The radio transmitting unit transmits to the external apparatus by radio the image information which is determined by the black image determining unit as the black image, as black image information.

An in-vivo image receiving apparatus according to still another aspect of the present invention is for receiving in-vivo image information from an in-vivo image acquiring apparatus which is taken into a body of a subject and which acquires the in-vivo image information in an illuminating state or in a non-illuminating state. The in-vivo image receiving apparatus includes an average value calculating unit that calculates an average value of pixel values of a predetermined determining area among the image information acquired in the non-illuminating state by the in-vivo image acquiring apparatus; a black image determining unit that determines whether the image information acquired in the non-illuminating state by the in-vivo image acquiring apparatus indicates a black image by comparing the average value calculated by the average value calculating unit with a predetermined threshold value; a black image storage unit that stores as black image information the image information determined as the black image by the black image determining unit; and a black image compensating unit that, based on the black image information stored in the black image storage unit, eliminates fixed pattern noises in the image information acquired in the illuminating state by the in-vivo image acquiring apparatus, and compensates the image information.

An in-vivo image receiving apparatus according to still another aspect of the present invention is for receiving in-vivo image information from an in-vivo image acquiring apparatus which is taken into a body of a subject and which acquires the in-vivo image information in an illuminating state or in a non-illuminating state. The in-vivo image receiving apparatus includes a peak detector detects a peak value of pixel values of pixels that constitute a predetermined determining area among the image information acquired in the non-illuminating state of the in-vivo image acquiring apparatus; a black image determining unit configured to determine whether the image information acquired in a non-illuminating state is the black image by comparing the peak value detected by the peak detector with a predetermined threshold value; a black image storage unit stores as black image information the image information determined as the black image by the black image determining unit; and an image compensating unit, based on the black image information stored in the black image storage unit, eliminates fixed pattern noises in the image information acquired in the illuminating state by the in-vivo image acquiring apparatus, and compensates the image information.

An in-vivo image displaying apparatus according to still another aspect of the present invention is for displaying image information acquired by an in-vivo image acquiring apparatus which is taken into a body of a subject and acquires in-vivo image information in an illuminating state or in a non-illuminating state. The in-vivo image displaying apparatus includes a black image pixel value averaging unit that calculates an average value of pixel values of a predetermined determining area among the image information acquired in a non-illuminating state by the in-vivo image acquiring apparatus; a black image determining unit that determines whether the image information acquired in the non-illuminating state indicates a black image by comparing the average value calculated by the black image pixel value averaging unit with a predetermined threshold value; a black image storage unit that stores as black image information the image information determined as the black image by the black image determining unit; and an image compensating unit that, based on the black image information stored in the black image storage unit, eliminates fixed pattern noises in the image information acquired in the illuminating state by the in-vivo image acquiring apparatus, and compensates the image information.

An in-vivo image displaying apparatus according to still another aspect of the present invention is for displaying image information acquired by an in-vivo image acquiring apparatus which is taken into a body of a subject and acquires in-vivo image information in an illuminating state or in a non-illuminating state. The in-vivo image displaying apparatus includes a peak detector that detects a peak value of pixel values of pixels that constitute a predetermined determining area among the image information acquired by the in-vivo image acquiring apparatus in a non-illuminating state; a black image determining unit that determines whether the image information acquired in the non-illuminating state indicates a black image by comparing the peak value detected by the peak detector with a predetermined threshold value; a black image storage unit that stores as black image information the image information determined as the black image by the black image determining unit; and a black image compensating unit that, based on the black image information stored in the black image storage unit, eliminates fixed pattern noises in the image information acquired in the illuminating state with the in-vivo image acquiring apparatus, and compensates the image information.

A noise eliminating method according to still another aspect of the present invention is for eliminating fixed pattern noises in in-vivo image information. The method includes acquiring the in-vivo image information in a non-illuminating state; calculating an average value of a predetermined determining area among the image information acquired in the non-illuminating state; determining whether the image information acquired in the non-illuminating state indicates a black image by comparing the calculated average value with a predetermined threshold value; acquiring the in-vivo image information in an illuminating state; and eliminating the fixed pattern noises in the image information acquired in the illuminating state and compensating the image information based on the image information determined as the black image.

A noise eliminating method according to still another aspect of the present invention is for eliminating fixed pattern noises in in-vivo image information. The method includes acquiring the in-vivo image information in a non-illuminating state; detecting a peak value of pixel values of pixels that constitute a predetermined determining area among the image information acquired in a non-illuminating sate; determining whether the image information acquired in the non-illuminating state indicates a black image by comparing the detected peak value with a predetermined threshold value; acquiring the in-vivo image information in an illuminating state; and eliminating the fixed pattern noises in the image information acquired in the illuminating state and compensating the image information based on the image information determined as the black image.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 17 is a flowchart showing a flow of operations of the capsule endoscope according to an exemplary variation.

DETAILED DESCRIPTION OF THE PREFERRED EMBODIMENTS

Exemplary preferred embodiments of the present invention will be explained in detail with reference to the accompanying drawings.

Figure 1:
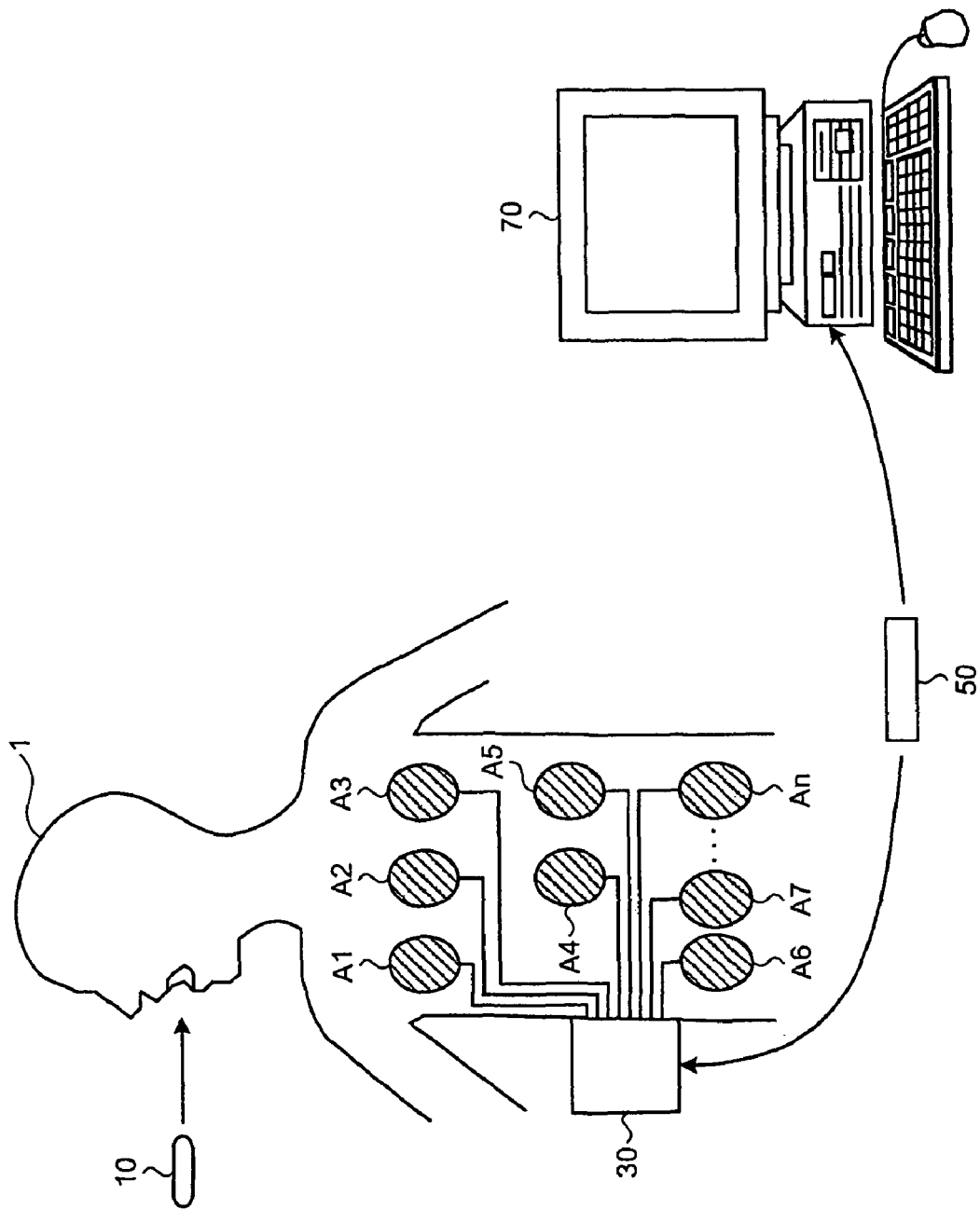
FIG. 1 is a schematic diagram of an overall configuration of an in-vivo image acquiring system according to a first embodiment of the present invention.

FIG. 1 is a schematic diagram of an overall configuration of an in-vivo image acquiring system according to the first embodiment of the present invention. As illustrated in FIG. 1, the in-vivo image acquiring system includes a capsule endoscope 10, a receiving apparatus 30, and a displaying apparatus 70. The capsule endoscope 10 is an in-vivo image acquiring apparatus which acquires in-vivo image information (in-vivo image information) of the subject 1. The receiving apparatus 30 is an in-vivo image receiving apparatus which receives the image information transmitted from the capsule endoscope 10 by radio. The displaying apparatus 70 is an in-vivo image displaying apparatus which displays the image information acquired by the capsule endoscope 10, based on the image information received by the receiving apparatus 30. For transferring the image information between the receiving apparatus 30 and the displaying apparatus 70, for example, a portable recording medium 50 may be used.

The capsule endoscope 10 is provided with an imaging function and a radio communication function. The capsule endoscope 10 is swallowed from the mouth of the subject 1 and taken into the body of the subject 1, and sequentially acquires inside the body cavity image information by travelling inside the body cavity, and transmits the acquired image information to outside the body via the radio communication.

The receiving apparatus 30 includes a plurality of receiving antennas A1 to An, the receiving apparatus 30 receives the image information that is transmitted from the capsule endoscope 10 via each of the receiving antennas A1 to An by radio. The receiving apparatus 30 is configured to be detachably attached by the portable recording medium 50 such as CompactFlash (registered trademark) and the like, and the receiving apparatus 30 sequentially stores the received image information in the portable recording medium 50. The receiving apparatus 30 accumulates the in-vivo image information of the subject 1 in chronological order in the portable recording medium 50.

The receiving antennas A1 to An are, for example, constituted by loop antennas as illustrated in FIG. 1, and are dispersedly arranged on the predetermined positions on the surface of the subject 1. Specifically, the receiving antennas A1 to An are dispersedly arranged on positions which correspond to the route the capsule endoscope 10 travels inside the subject 1. The receiving antennas A1 to An may be dispersedly arranged on a jacket to be worn by the subject 1. In such a case, the receiving antennas A1 to An are arranged on predetermined positions which correspond to the route the capsule endoscope 10 travels inside the subject 1 as the subject 1 wears the jacket. At least one receiving antenna may be arranged on one subject 1; the numbers of the antennas are not limited.

The displaying apparatus 70 is realized by the general-purpose computers such as a workstation or personal computer, and is configured in such a manner that the portable recording medium 50 is detachably attached to the displaying apparatus 70. The displaying apparatus 70 reads in the image information stored in the portable recording medium 50, and displays the read image information, as images, on displays such as LCD and ELD. Moreover, the displaying apparatus 70 arbitrarily writes the information concerning the subject 1 on the portable recording medium 50. The displaying apparatus 70 may be structured to output the image to other media with printers and the like.

Figure 2:
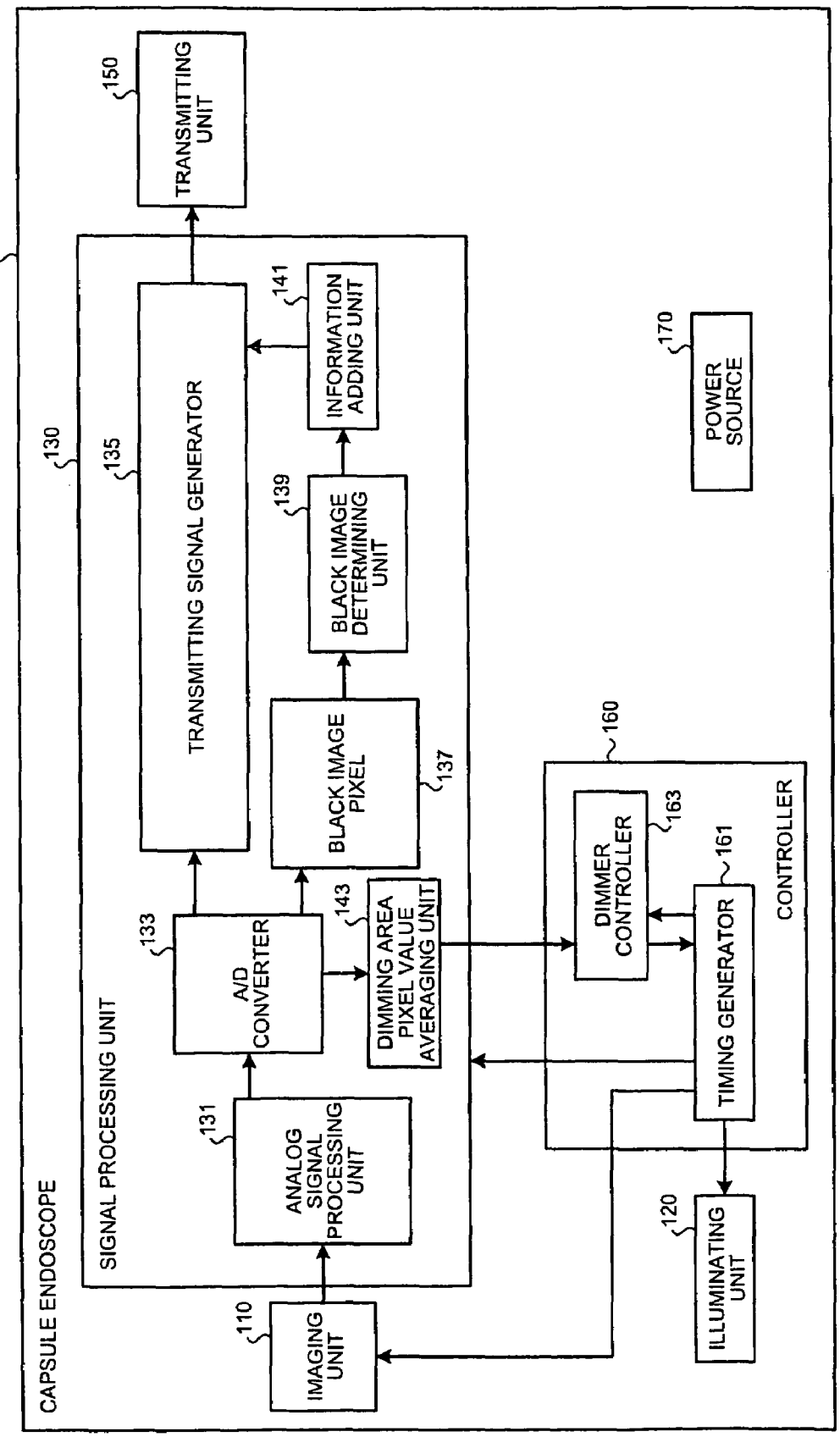
FIG. 2 is a functional block diagram of a capsule endoscope according to the first embodiment.

The configuration of the capsule endoscope 10 according to the first embodiment will be explained next. FIG. 2 is a functional block diagram of the capsule endoscope 10. As illustrated in FIG. 2, the capsule endoscope 10 includes an imaging unit 110, an illuminating unit 120, a signal processing unit 130, a transmitting unit 150, a control unit 160, and a power source 170 which supplies the power to each of the units that constitutes the capsule endoscope 10.

The imaging unit 110 includes the image sensor such as CMOS or CCD, and an imaging lens which makes the incident light form an image on the image pickup device. The imaging unit 110 conducts the imaging operation which takes the in-vivo images of the subject 1 by outputting an analog signal in accordance with the intensity of the incident light. Specifically, the imaging unit 110 conducts the imaging operation in supply timing of the imaging unit driving pulse from a timing generator 161 which will be described later.

The illuminating unit 120 includes, for example, a light-emitting device such as an LED and a driving circuit of the light-emitting device, and conducts the illuminating operation that illuminates the imaging regions of which images are taken by the imaging unit 110. Specifically, the illuminating unit 120 starts the illuminating operation in supply timing of the illuminating unit driving pulse from a timing generator. Then the illuminating unit 120 emits an amount of illuminating light which is adjusted by a dimmer controller 163 (explained later) by illuminating the imaging regions for a time equivalent to the pulse width of the supplied illuminating unit driving pulse.

The signal processing unit 130 includes an analog signal processing unit 131, an A/D converter 133, and a transmitting signal generator 135, and generates transmitting signals by giving necessary processes to the images taken by the imaging unit 110. The analog signal processing unit 131 conducts analog signal processes such as the correlated double sampling or amplification to the analog signals input from the imaging unit 110. The A/D converter 133 converts the analog signals, input from the analog signal processing unit 131, into the digital signals. The converted digital signals are output to the transmitting signal generator 135, a black image pixel value averaging unit 137 which will be described later, and the dimming area pixel value averaging unit 143.

The transmitting signal generator 135 generates transmitting signals for transmitting, by radio, the acquired image information to outside the body based on the digital signals input from the A/D converter 133. For example, the transmitting signal generator 135 regards a sheet of image information as one frame, and adds the vertical synchronization signal in the front of the frame, and generates the transmitting signals by adding the horizontal synchronization signal in the front of the constituent data of each line, and outputs the transmitting signals to the transmitting unit 150.

Figure 3:
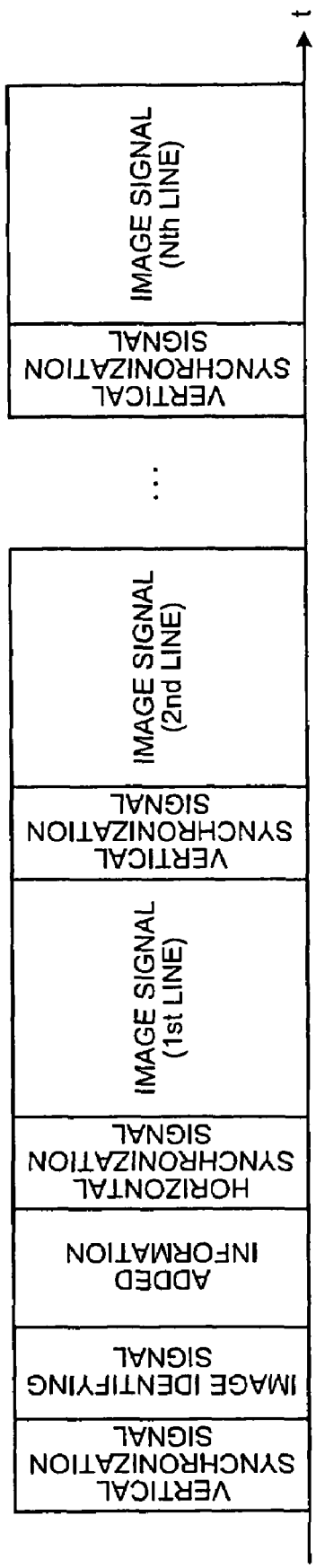
FIG. 3 is an example of transmitting signal generated by the transmission signal generator according to the first embodiment.

FIG. 3 illustrates an example of the transmitting signal generated by the transmitting signal generator 135. As illustrated in FIG. 3, the transmitting signals are constituted as the vertical synchronization signal, the field that indicates the image identifying information and the added information, and the image signals that correspond to the constituent data of each line that includes the horizontal synchronization signal are distributed. The image identifying information is information that is added when the image identifying information is input from the information adding unit 141 which will be described later. The image identifying information is acquired by a black image acquiring operation which will be described later, and used for identifying the image information that is determined as the black image by a black image determining unit 139 which will be described later. Such information, for example, as the model name, serial number, and the white balance coefficient of the capsule endoscope 10 are arbitrarily set as the added information. The transmitting signals are input to the transmitting unit 150 and transmitted to the receiving apparatus 30 located at the outside of the body by radio. The receiving apparatus 30, which has received the transmitting signals, detects the front part of the image with the vertical synchronization signal, processes each of the image signals by detecting the front of the image signal of each line based on the horizontal synchronization signals, and acquires the image information.

The signal processing unit 130 includes the black image pixel value averaging unit 137, the black image determining unit 139, and an information adding unit 141, and determines whether the image information acquired by the black image acquiring operation is the black image or not.

The black image pixel value averaging unit 137 regards, the whole area that is acquired by the black image acquiring operation, as the determining area, and calculates the average value of the pixel value of the image information. For example, the black image pixel value averaging unit 137 calculates the simple average value by integrating the pixel value of each pixel that constitutes the image information, and dividing the result of the integration by the number of pixels. The calculated average value is output to the black image determining unit 139.

The black image determining unit 139 compares the average value input from the black image pixel value averaging unit 137 with a black image standard value that is predetermined as the threshold value, as a result of the comparison, if the input average value is equal to the black image standard value or less, the black image determining unit 139 determines the image information is the black image. Close to black and small enough value is set as the black image standard value. The result of the determination is output to the information adding unit 141.

The information adding unit 141 generates the image identifying information that corresponds to the result of the determination input from the black image determining unit 139. The image identifying information is generated as, for example, flag information that indicates whether it is the black image or not, and is output to the transmitting signal generator 135. Consequently, if the image information is determined as the black image by the black image determining unit 139, the information indicating the image information is the black image is added to the transmitting signals that are generated with the transmitting signal generator 135.

The signal processing unit 130 is provided with the dimming area pixel value averaging unit 143, and outputs the calculated average value to the dimmer controller 163 (explained later). Specifically, a target dimming area is predetermined; the dimming area pixel value averaging unit 143 calculates the average value of the pixel value that is included in the dimming area among the in-vivo image information acquired by the in-vivo image acquiring operation (explained later). For example, the dimming area pixel value averaging unit 143 calculates the weighted average value of the RGB value of each pixel that constitutes the dimming area and obtains the average luminance of the dimming area.

The transmitting unit 150 includes: a transmitting circuit that generates radio signals by conducting, as needed, modulation processing and the like toward the transmitting signals input from the signal processing unit 130; and an antenna for transmitting the generated radio signals to the outside, and transmits the transmitting signals to the outside by radio.

The control unit 160 controls each of the units that constitutes the capsule endoscope 10, and controls the overall operations of the capsule endoscope 10 as a whole. The control unit 160 includes the timing generator 161 and the dimmer controller 163.

The timing generator 161 generates the drive timings for the imaging unit 110 and illuminating unit 120. The timing generator 161 controls the in-vivo image acquiring operation in which the imaging unit 110 conducts the imaging operation in the state the illuminating unit 120 is conducting the illuminating operation (illuminating state). Alternatively, the timing generator 161 controls the in-vivo image acquiring operation in which the imaging unit 110 conducts the imaging operation in the state the illuminating unit 120 is not conducting the illuminating operation (non-illuminating state).

Figure 4:
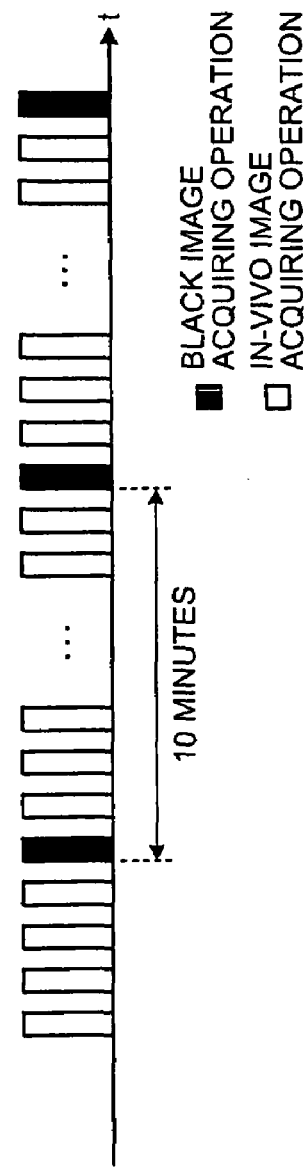
FIG. 4 is an explanatory diagram for explaining timings of the in-vivo image information acquiring operation and black image acquiring operation according to the first embodiment.

FIG. 4 is an explanatory diagram for explaining timings of the in-vivo image information acquiring operation and black image acquiring operation. As illustrated in FIG. 4, the imaging operations by the imaging unit 110 are conducted at a predetermined time interval, for example at 0.5 second interval, among this, the imaging operations in the non-illuminating state (black image acquiring operation) are conducted, for example every 10 minutes, and then the image information is acquired. Whether the acquired image information is black image or not is determined by the black image determining unit 139. Meanwhile, in other timings than the black image acquiring operation, the imaging operations are conducted in the illuminating state (in-vivo image acquiring operation), and the in-vivo image information is acquired.

Specifically, the timing generator 161 conducts the following controls. More specifically, the timing generator 161 controls the imaging operation of the imaging unit 110 by supplying the imaging unit driving pulse to the imaging unit 110 at an interval of 0.5 second. In the timing of the in-vivo image acquiring operation, the timing generator 161 controls the illuminating operation of the illuminating unit 120 by supplying the illuminating unit driving pulse to the illuminating unit 120 immediately before supplying the imaging start pulse. At the same time, the timing generator 161 increases or decreases the pulse width of the illuminating unit driving pulse in accordance with the illuminating time input from the dimmer controller 163 (explained later), and the timing generator 161 specifies the operation start timing by the rising edge of the pulse, and specifies the operation end timing by the trailing edge of the pulse.

The timing generator 161 synchronizes the processing of each unit with the supplying timing of the imaging unit driving pulse by driving each unit that constitute the signal processing unit 130 based on the supplying timing of the imaging unit driving pulse.

The dimmer controller 163 conducts the dimmer control to adjust the amount of luminescence of the illuminating light that is emitted by the illuminating unit 120. Specifically, the dimmer controller 163 compares the average value input from the dimming area pixel value averaging unit 143 with the standard luminance value predetermined as the threshold value, and then determines the brightness of the dimming area in the in-vivo image information acquired by the in-vivo image acquiring operation. The luminance value in which the contents of the image are easily visible for the user is set as the standard luminance value. The illuminating time of the illuminating unit 120 is calculated based on the result of the comparison, and the calculated illuminating time is output to the timing generator 161. The quality level of the acquired in-vivo image is kept constant by adjusting the amount of luminescence of the illuminating light in the in-vivo image acquiring operation for the next time based on the brightness of the dimming area in the in-vivo image information acquired this time. For example, if the brightness of the dimming area in the in-vivo image information acquired this time is too bright, the illuminating time with the illuminating unit 120 for the next time will be set shortened, on the other hand, if brightness is too dark the illuminating time with the illuminating unit 120 for the next time will be set extended. The method of adjusting the amount of luminescence of the illuminating light is not limited to adjusting the illuminating time; for example, the amount of luminescence may be adjusted by adjusting the electric current value supplied to light emitting devices that constitute the illuminating unit 120. The amount of luminescence may be adjusted by changing the luminance of the light emitting devices.

As explained above, the capsule endoscope 10 according to the first embodiment, the imaging unit 110 conducts the imaging operation at a predetermined time interval in accordance with the control by the timing generator 161. However, in the timing of black image acquiring operation, the imaging unit 110 conducts the imaging operation in the state that the illuminating unit 120 does not conduct the illuminating operation, and then acquires the in-vivo image information of the subject 1 that is taken in the non-illuminating state. While the signal processing unit 130 generates the transmitting signals based on the image information acquired through the black image acquiring operation, the black image pixel value averaging unit 137 calculates the average value of the pixel value of the acquired image information. The black image determining unit 139 determines whether the image information is the black image or not, the information adding unit 141 generates the image identifying information that corresponds to the result of the determination and adds the image identifying information to the transmitting signals generated by transmitting signal generator 135. The transmitting unit 150 transmits the generated transmitting signals to outside the body by radio.

Meanwhile, in the timing of the in-vivo image acquiring operation, the imaging unit 110 conducts the imaging operation in the state the illuminating unit 120 is conducting the illuminating operation, acquires the in-vivo image information by imaging inside the body of the subject 1 in the illuminating state. The signal processing unit 130 generates the transmitting signals based on the in-vivo image information acquired through the in-vivo image acquiring operation, and the transmitting unit 150 transmits the transmitting signals to outside the body by radio. The dimming area pixel value averaging unit 143 calculates the average luminance value of the predetermined dimming area among the acquired in-vivo image information. The dimmer controller 163 determines the brightness of the dimming area, and decides the illuminating time by the illuminating unit 120 for the next time based on the determined brightness.

The image information wirelessly transmitted by the capsule endoscope 10 is received by the receiving apparatus 30. In the receiving apparatus 30, if the received image information is the black image, the image information is stored as the black image information in an embedded memory such as RAM. Meanwhile, if the received image information is the in-vivo image information, the in-vivo image information is sequentially stored in the portable recording medium 50, however, as a preprocessing of storage, the fixed pattern noises in the in-vivo image information are eliminated based on the black image information stored in the embedded memory, and the image compensation is conducted. Specifically, the fixed pattern noises contained in the in-vivo image information are eliminated by subtracting the black image information from the in-vivo image information. The in-vivo image information stored in the portable recording medium 50 at the receiving apparatus 30 is displayed as the image on the displaying apparatus 70. If the receiving apparatus 30 receives new black image information from the capsule endoscope 10, the receiving apparatus 30 rewrites the black image information stored in the embedded memory with the new black image information.

According to the first embodiment explained above, the capsule endoscope 10 is capable of determining whether the image information is the black image or not by calculating the average value of the pixel value of the image information acquired in the non-illuminating state. The capsule endoscope 10 is capable of transmitting the image information by radio, as the black image, to the receiving apparatus 30 of outside the body by adding the image identifying information that indicates the image information is the black image. Therefore, the capsule endoscope 10 is capable of securely acquiring the black image which is necessary for eliminating the fixed pattern noises in the in-vivo image information. Consequently, the receiving apparatus 30 can eliminate the fixed pattern noises in the in-vivo image information acquired in the illuminating state, and store the in-vivo image information in the portable recording medium 50 after conducting appropriate image compensation to the in-vivo image information. The black image acquiring image acquiring operation is conducted at a predetermined time interval and the black images are acquired in many positions in the body. Since the fixed pattern noises are influenced by environments such as temperature, it is possible to conduct more appropriate image compensation by acquiring the black image in many positions in the body as explained above.

In the first embodiment, although it is explained that the receiving apparatus 30 conducts the process concerning the fixed pattern elimination, the displaying apparatus 70 may conduct the process concerning the fixed pattern elimination instead of the receiving apparatus 30. In this case, the receiving apparatus 30 stores the image information, which is received together with the image identifying information and the added information, in the portable recording medium 50 sequentially in order of receipt. The displaying apparatus 70 sequentially reads out the image information stored in the portable recording medium 50, if the read out information is the black image, the displaying apparatus 70 stores the black image as the black image information in the embedded memory such as RAM. On the other hand, if the read out information is the in-vivo image information, the displaying apparatus 70 displays the in-vivo image information as images, however as a preprocessing of the image display, the displaying apparatus 70 eliminates the fixed pattern noises in the in-vivo image information based on the black image information stored in the embedded memory, and conducts the image compensation. If the displaying apparatus 70 reads out the image information of the black image anew, the displaying apparatus 70 rewrites the black image information stored in the embedded memory with the new black image information. According to an exemplary variation of the present embodiment, the displaying apparatus 70 can appropriately eliminate the fixed pattern noises in the in-vivo image information acquired in the illuminating state, and display the image after conducting appropriate image compensation toward the in-vivo image information.

Figure 5:
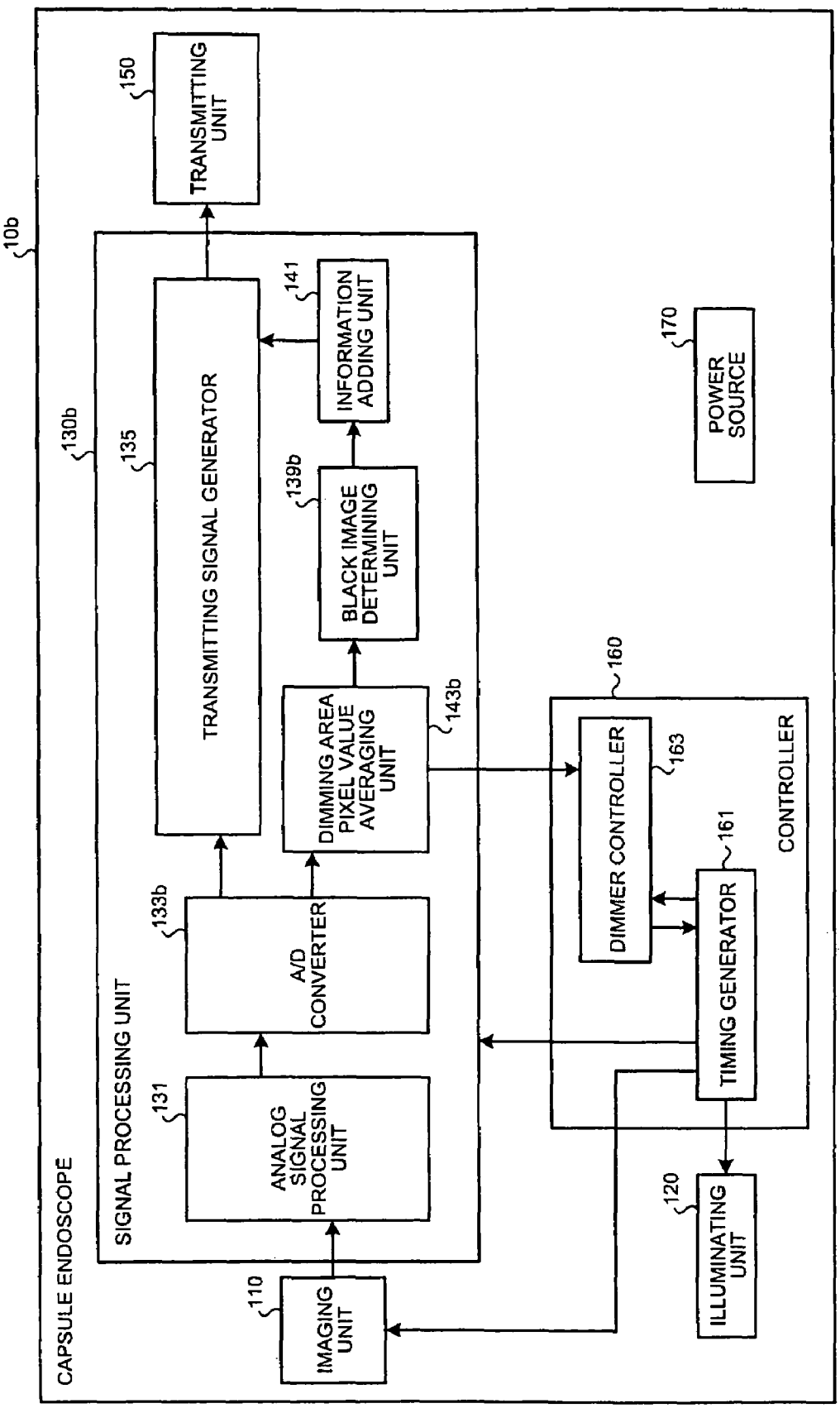
FIG. 5 is a functional block diagram of the capsule endoscope according to an exemplary variation of the first embodiment.

In the first embodiment, the average value of the pixel value is calculated on the assumption that the whole area of the image information acquired by the black image acquiring operation is the determining area. Alternatively, it is possible to determine whether the image information is the black image or not, by calculating the average value of the pixel value that is included in the dimming area, on the assumption that the dimming area, which is regarded as the target for calculating the average value by the dimming area pixel value averaging unit 143, is the determining area. In this case, it is possible to determine whether the image information acquired using the average value calculated by the dimming area pixel value averaging unit 143 is the black image or not. In this case it is possible to simplify the structure of the capsule endoscope 10 because the black image pixel value averaging unit 137 is not needed. FIG. 5 is the functional block diagram of the capsule endoscope 10b in this case. The same referential marks are put to the similar parts as the first embodiment.

As illustrated in FIG. 5, the capsule endoscope 10b according to the exemplary variation is provided with a signal processing unit 130b. The signal processing unit 130b includes, an analog signal processing unit 131, an A/D converter 133b, a transmitting signal generator 135, a black image determining unit 139b, an information adding unit 141, and a dimming area pixel value averaging unit 143b. In the signal processing unit 130b, the analog signals output from the imaging unit 110 is analog signal processed with the analog signal processing unit 131, and converted into digital signals with the A/D converter 133b. The converted digital signals are output to the transmitting signal generator 135 and dimming area pixel value averaging unit 143b. The transmitting signals for transmitting to outside the body by radio are generated in the transmitting signal generator 135; the acquired image information is transmitted to the receiving apparatus 30 by radio with the transmitting unit 150.

The dimming area pixel value averaging unit 143b, in a similar way as the first embodiment, calculates the weighted average value of the RGB value of each pixel that constitutes the predetermined dimming area and obtains the average luminance of the dimming area. However, according to the present exemplary variation, the average value calculated based on the in-vivo image information acquired by the in-vivo image acquiring operation is output to the dimmer controller 163, and the average value calculated based on the image information acquired by the black image acquiring operation is output to the black image determining unit 139b.

The black image determining unit 139b compares the average value input from the dimming area pixel value averaging unit 143b with the black image standard luminance value predetermined as the threshold value, as a result of the comparison, if the average value input is equal to the black image standard luminance value or less, the image information is determined as the black image. A dark enough value is set as the black image standard luminance value. The result of the determination is output to the information adding unit 141.

According to the present exemplary variation, it is possible to determine whether the image information taken in the non-illuminating state is the black image or not by using the output value of the dimming area pixel value averaging unit 143b which is provided to the capsule endoscope 10b for controlling the adjustment of the amount of illuminating light that is emitted from the illuminating unit 120.

Figure 6:
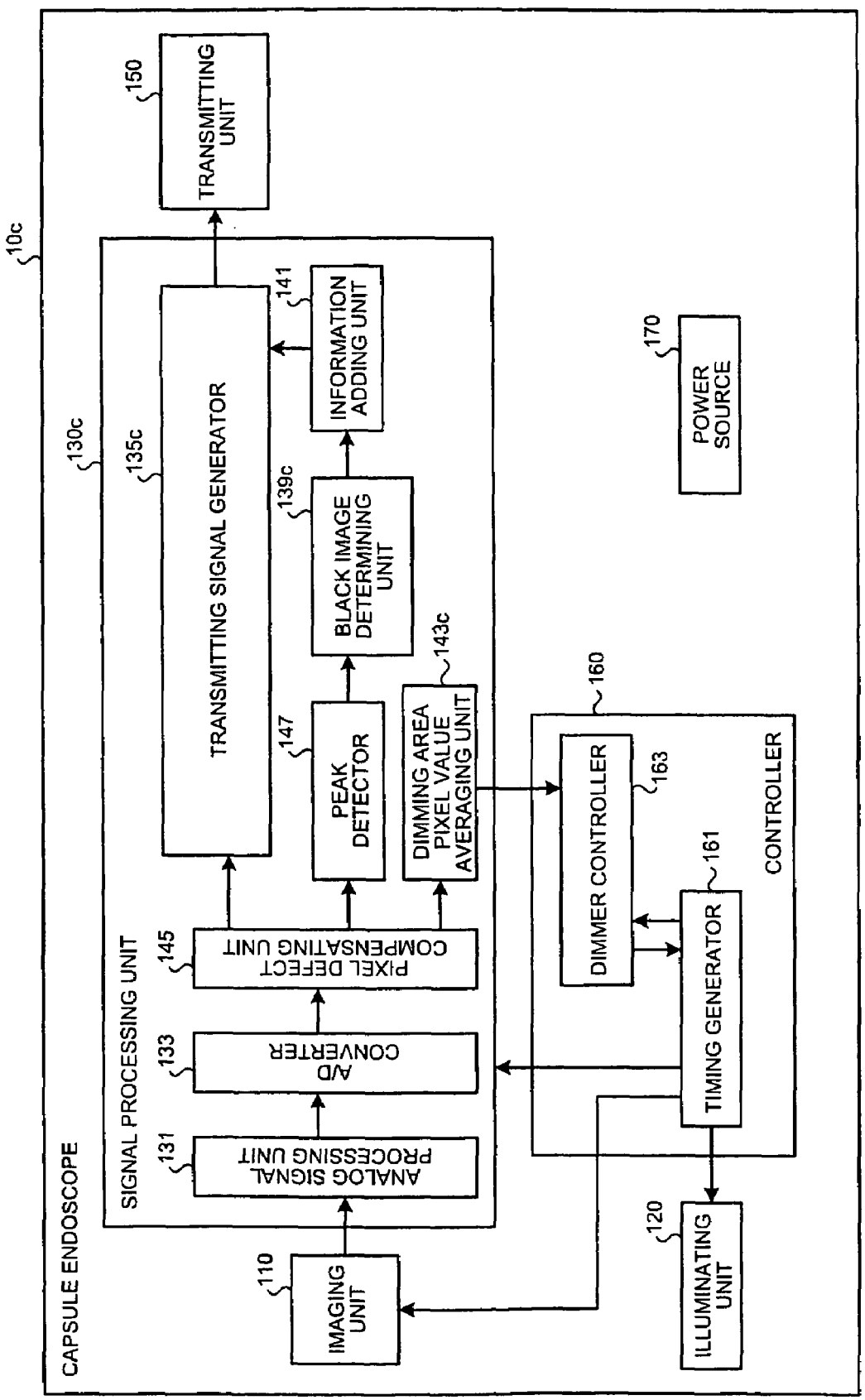
FIG. 6 is a functional block diagram of a capsule endoscope according to a second embodiment.

A second embodiment will be explained next. FIG. 6 is a functional block diagram for explaining the capsule endoscope 10c according to the second embodiment. The same referential marks are put to the similar configuration as the first embodiment.

As illustrated in FIG. 6, the capsule endoscope 10c according to the second embodiment is provided with a signal processing unit 130c. The signal processing unit 130c includes, an analog signal processing unit 131, an A/D converter 133, a pixel defect compensating unit 145, a transmitting signal generator 135c, a peak detector 147, a black image determining unit 139c, an information adding unit 141, and a dimming area pixel value averaging unit 143c. In the signal processing unit 130c, the analog signals input from the imaging unit 110 is analog signal processed with the analog signal processing unit 131, and converted into digital signals with the A/D converter 133. The converted digital signals are output to the pixel defect compensating unit 145.

The pixel defect compensating unit 145 detects the pixel defects in the acquired image information based on the digital signals input from the A/D converter 133, and compensates the pixels having pixel defects. The pixel defects, in this case, are attributed to the crystal quality of the image sensor that constitutes the imaging unit 110. Specifically, for example, the pixel defects are attributed to deterioration with time of the crystal itself, and effect of the environmental change, and the pixel defects are appear as white dots or black dots on the image. The pixel defect compensating unit 145 compares the pixel value of each pixel (a first pixel) with the pixel value of the pixel (a second pixel) having the same color, which is horizontally adjacent to the first pixel. If the difference between the first and second pixel value is the same as the predetermined threshold value or over, the pixel defect compensating unit 145 detects the first pixel as defective. The pixel defect compensating unit 145 compensates the pixel defects of the first pixel by replacing the pixel value of the first pixel with a value that corresponds to the pixel value of the second pixel. Alternatively, the pixel defect compensating unit 145 detects the pixel defects of the first pixel by comparing the pixel value of the first pixel with the pixel value of the pixel (a third pixel) having the same color and is vertically adjacent to the first pixel. The pixel defect compensating unit 145 compensates the pixel defects of the first pixel by replacing the pixel value of the first pixel with a value that corresponds to the pixel value of the third pixel. The compensated image information is output to the transmitting signal generator 135c, the peak detector 147, and the dimming area pixel value averaging unit 143c.

The transmitting signal generator 135c generates the transmitting signals for transmitting the image information, of which pixel defects are compensated with the pixel defect compensating unit 145, to outside the body by radio. Moreover, if the image identifying information is input from the information adding unit 141, the transmitting signal generator 135c adds the image identifying information to the generated transmitting signals. The generated transmitting signals are transmitted to outside the body with the transmitting unit 150 by radio, and the acquired image information is transmitted to the receiving apparatus 30 by radio.

The peak detector 147 regards the whole area of the image information acquired by the black image acquiring operation as the determining area, and detects the peak value of the pixel value of each pixel, which constitutes the image information. The detected peak value is output to the black image determining unit 139c.

The black image determining unit 139c compares the peak value input from the peak detector 147 with a black image standard peak value which is predetermined as threshold value, and as a result of the comparison, if the input peak value is equal to the black image standard peak value or less, the black image determining unit 139c determines the image information is the black image. Close to black and small enough value is set as the black image standard value. The result of the determination is output to the information adding unit 141.

According to the capsule endoscope 10c structured as mentioned above, the imaging unit 110 conducts the imaging operation at a predetermined time interval in accordance with the control by the timing generator 161 in a similar manner as the first embodiment. In the timing of the black image acquiring operation, the imaging unit 110 conducts the imaging operation in the state that the illuminating unit 120 does not conduct the illuminating operation, and then acquires the in-vivo image information of the subject 1 taken in the non-illuminating state. While the signal processing unit 130c compensates the pixel defects of the image information taken by the black image acquiring operation, and generates the transmitting signals based on the compensated image information, the peak detector 147 calculates the peak value of the pixel value of each pixel which constitutes the acquired image information. Then the black image determining unit 139c determines whether the image information is the black image or not, the information adding unit 141 generates the image identifying information, which corresponds to the result of the determination by the black image determining unit 139c, adds the identifying information to the transmitting signals that are generated with the transmitting signal generator 135c. The transmitting unit 150 transmits the generated transmitting signals to outside the body by radio.

Meanwhile, in the timing of the in-vivo image acquiring operation, the imaging unit 110 conducts the imaging operation in the state the illuminating unit 120 is conducting the illuminating operation, acquires the in-vivo image information by imaging inside the body of the subject 1 in the illuminating state. The signal processing unit 130c compensates the pixel defects of the in-vivo image information acquired through the in-vivo image acquiring operation, and generates the transmitting signals based on the compensated in-vivo image information. The transmitting unit 150 transmits the generated transmitting signals to outside the body by radio.

According to the second embodiment as explained above, the capsule endoscope 10c can determine whether the image information is the black image or not by detecting the peak value of the pixel value of each pixel that constitutes the image information. The capsule endoscope 10c can transmit, by radio, the image information to the receiving apparatus 30 of outside the body as the black image, by adding the image identifying information which indicates the image information is the black image, to the image information determined as the black image. Therefore the capsule endoscope 10c can securely acquire the black image which is necessary for eliminating the fixed pattern noises in the in-vivo image information. As a result, the capsule endoscope 10c can, in the receiving apparatus 30 or displaying apparatus 70, appropriately eliminate the fixed pattern noises in the in-vivo image information which is taken in the illuminating state, and can conduct appropriate image compensation toward the in-vivo image information.

Although in the aforementioned first and second embodiments, the capsule endoscopes each having a single imaging unit was explained, the embodiments also can be applied to the capsule endoscopes having a plurality of imaging units. In this case, the capsule endoscope adds the information, which identifies the imaging unit that has acquired the corresponding image information, to the transmitting signals for transmitting the acquired image information to the receiving apparatus 30, and then transmits the transmitting signals to the receiving apparatus 30 by radio. In the meantime, for example, the receiving apparatus 30, based on the received transmitting signals, identifies the imaging unit that has acquired the corresponding image information. The receiving apparatus 30 stores the image information in the embedded memory classifying the image information based on the imaging unit that has acquired the image information. After then, in the case the receiving apparatus 30 receives the image information; the receiving apparatus 30 firstly identifies the imaging unit that has acquired the in-vivo image information. The receiving apparatus 30 eliminates the fixed pattern noise in the in-vivo image information based on the black image acquired with the identified imaging unit, and conducts the image compensation.

In the aforementioned first and second embodiments, the capsule endoscope is configured to transmit the image information, acquired by the black image acquiring operation, to the receiving apparatus 30, by adding the image identifying information based on the determination whether the image information is the black image or not. Meanwhile, the capsule endoscope may be configured to transmit exclusively image information that is determined to be the black image, without sending the image information that is determined not to be the black image. By this, it is possible to reduce the electricity consumption of the capsule endoscope.

In the aforementioned first and second embodiments, the capsule endoscope is configured to transmit the image identifying information, which is generated for identifying the image information that is determined as the black image, together with the image information to the receiving apparatus 30. Alternatively, the capsule endoscope may be configured to predetermined the patterns for the in-vivo image and for the black image as the vertical synchronization signals, and to identify the corresponding image information based on the patterns of the vertical synchronization signals. In this case, the capsule endoscope transmits the transmitting signals that are set with the vertical synchronization signals for the in-vivo image if the image information to be transmitted is the in-vivo image information, or transmits the transmitting signals that are set with the vertical synchronization signals for the black image if the image information to be transmitted is determined to be the black image information. In the meantime, the receiving apparatus 30 determines the patterns of the vertical synchronization signals of the received image signals, and distinguishes whether the image information is the in-vivo image information or the black image.

A third embodiment will be explained next. The third embodiment is an embodiment in which processes related to the black image determination and fixed pattern noise elimination, which are explained in the first embodiment, are conducted with the receiving apparatus.

Figure 7:
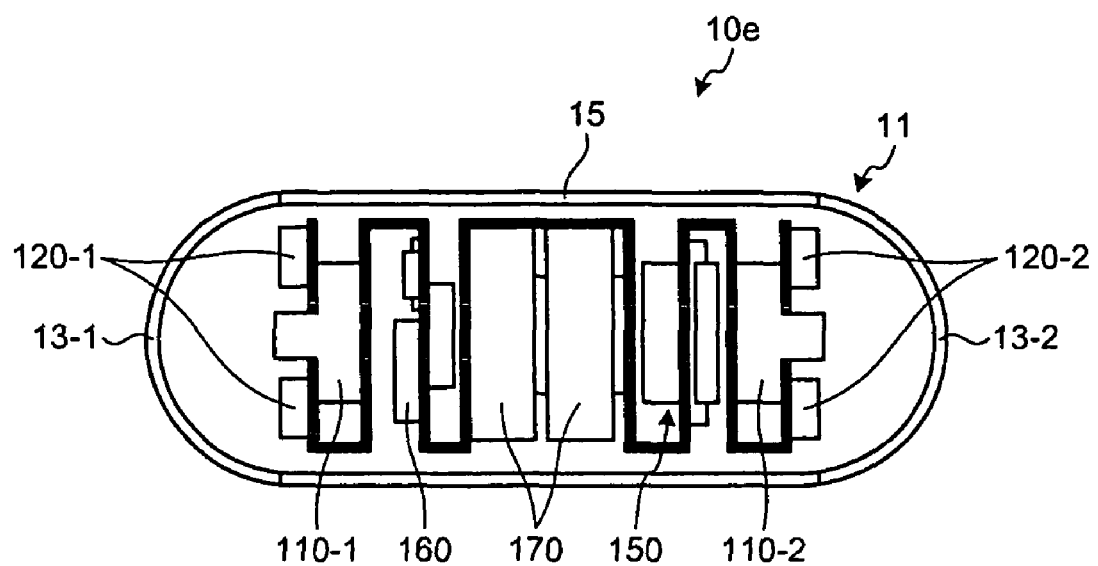
FIG. 7 is a schematic internal view a capsule endoscope according to a third embodiment.

First, the configuration of the capsule endoscope according to the third embodiment will be explained. FIG. 7 is a schematic view of the capsule endoscope 10e according to the third embodiment. The same referential marks are put to the similar configuration as the first embodiment. The capsule endoscope 10e of the present embodiment is provided with the imaging unit and illuminating unit at both ends of the capsule endoscope 10e. The capsule endoscope 10e is capable of acquiring the in-vivo image information of both the front and rear with respect to the travelling direction of the capsule endoscope 10e. Specifically, as illustrated in FIG. 7 the capsule endoscope 10e includes, in a capsule-shaped case 11, imaging units 110-1, 110-2, illuminating units 120-1, 120-2, a transmitting unit 150, a control unit 160, and a power source 170. Hereinafter the imaging unit 110-1 will be described as the front imaging unit, and the imaging unit 110-2 will be described as the rear imaging unit. The illuminating unit 120-1 will be described as the front illuminating unit, and the illuminating unit 120-2 will be described as the rear illuminating unit The case 11 is swallowable by human in size, and is formed as the substantially semispherical top covers 13-1, and 13-2, and a cylindrical body cover 15 are combined together. The top covers 13-1 and 13-2 are made of a transparent material and function as optical windows. Specifically, in inside the case 11, the front imaging unit 110-1 and the front illuminating unit 120-1 are disposed facing the top cover 13-1. The top cover 13-1 transmits the illumination light emitted from the front illuminating unit 120-1 to outside the case 11, and guides the reflected light into inside the case 11. In the same manner, in inside the case 11, the rear imaging unit 110-2 and the rear illuminating unit 120-2 are disposed facing the top cover 13-2. The rear cover 13-2 transmits the illumination light emitted from the rear illuminating unit 120-2 to outside case, and guides the reflected light into inside the case 11.

In the capsule endoscope 10e, a transmitting signal generator (not illustrated) generates transmitting signals for transmitting the acquired image information to outside the body by radio. The capsule endoscope 10e adds the imaging unit identifying information to the acquired image information. The imaging unit identifying information is to identify the imaging unit in which the imaging operation is conducted. Furthermore, the transmitting signal generator generates the transmitting signals to which illuminating state identifying information and adding information are added. The illuminating state identifying information and adding information indicate whether the image information is the in-vivo image information acquired in the illuminating state or the black image information acquired in the non-illuminating state. The generated transmitting signals are transmitted to the receiving unit 30e of outside the body with the transmitting unit 150.

Figure 8:
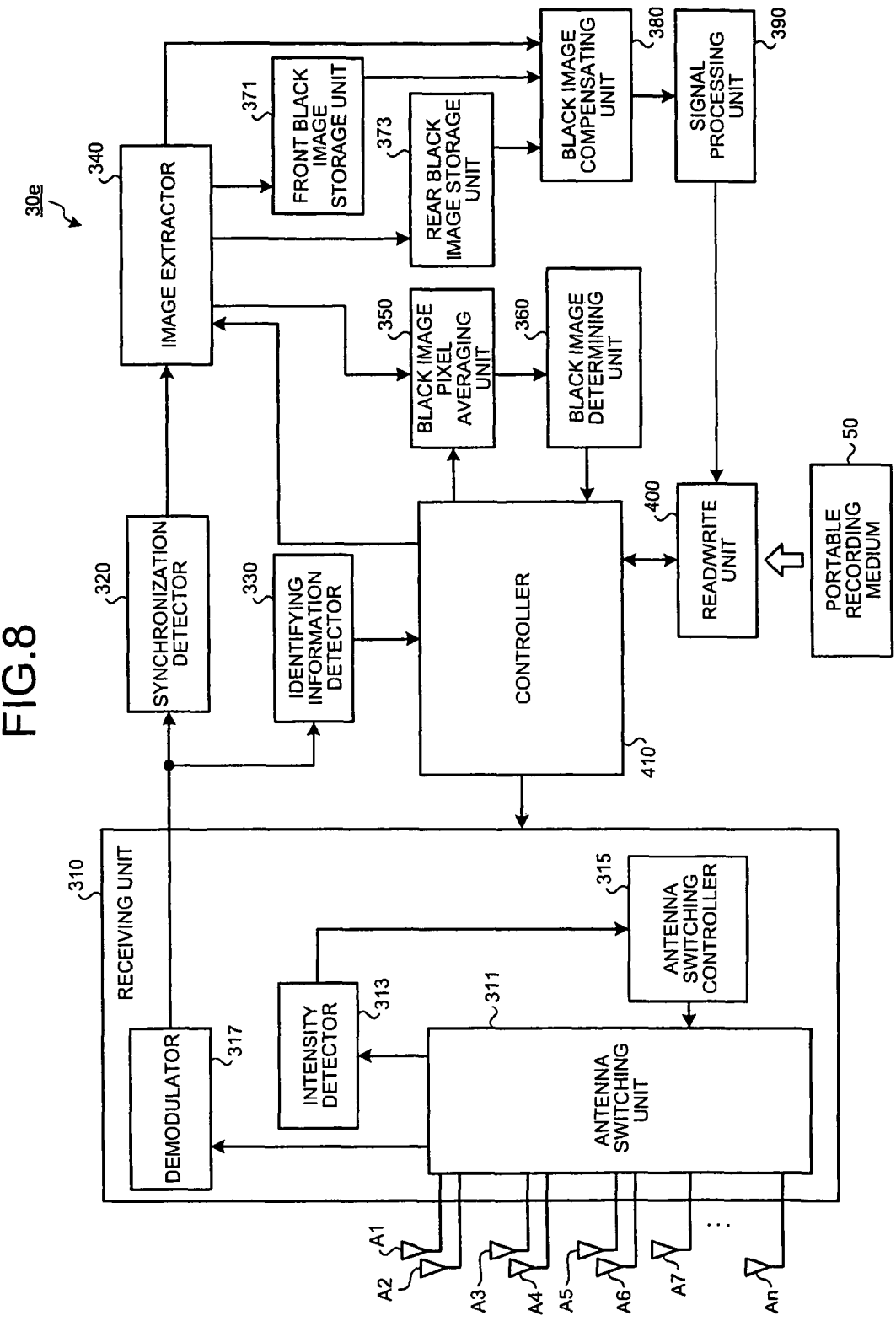
FIG. 8 is a functional block diagram of a receiving apparatus according to the third embodiment.

The structure of the receiving apparatus according to the third embodiment will be explained next. FIG. 8 is a functional block diagram of the receiving apparatus 30e according to the third embodiment. As illustrated in FIG. 8, the receiving apparatus 30e includes, a receiving unit 310, a synchronization detector 320, an identifying information detector 330, an image extractor 340, a black image pixel averaging unit 350, a black image determining unit 360, a black image compensating unit 380, a signal processing unit 390, a read/write unit 400, and a control unit 410 that controls each of the units that constitutes the receiving apparatus 30e, and controls the overall operations of the receiving apparatus 30e as a whole.

The receiving unit 310 includes receiving antennas A1 to An, an antenna switching unit 311, an intensity detector 313, an antenna switching controller 315, and a demodulator 317, and receives radio signals from the capsule endoscope 10e.

The antenna switching unit 311 switches the antenna that receives radio signals from the capsule endoscope 10e to one of any receiving antennas A1 to An. The antenna switching unit 311 is connected to the receiving antennas A1 to An via cables. The radio signals, received from the capsule endoscope 10e via the receiving antenna that is selected by the switching unit 311 among from the receiving antennas A1 to An, are output to the demodulator 317. Furthermore, the antenna switching unit 311 outputs the radio signals, received from each of the receiving antennas A1 to An, to the intensity detector 313.

The intensity detector 313 detects the receiving intensity of the radio signals received from the capsule endoscope 10e via the switching unit 311, and outputs the detected receiving intensity to the antenna switching controller 315.

The antenna switching controller 315 selects the most suitable receiving antenna, for receiving the radio signals from the capsule endoscope 10e, among from the receiving antennas A1 to An. Specifically, the antenna switching controller 315 selects, among from the receiving antennas A1 to An, the receiving antenna which indicates the maximum receiving intensity of the radio signals received from the capsule endoscope 10e. The antenna switching controller 315 controls the switching operation of the antenna switching unit 311 so that the antenna switching unit 311 switches to the selected receiving antenna.

The demodulator 317 conducts the demodulating processing to the radio signals received from the capsule endoscope 10e via the antenna switching unit 311, and demodulates to the image signals. The image signals correspond to the transmitting signals generated in the capsule endoscope 10e. For example, the image signals include, the image information taken with the capsule endoscope 10e, the vertical synchronization signals that are included in each frame, the horizontal synchronization signals that are included in each line of the frame, the imaging unit identifying information, and the illuminating state identifying information.

The demodulator 317 outputs the demodulated image signals to the synchronization detector 320 and identifying information detector 330.

The synchronization detector 320 detects, for each frame, the vertical synchronization signals that are included in the image signal demodulated with the demodulator 317.

The identifying information detector 330 determines the illuminating state identifying information that is included in the image information demodulated with the demodulator 317, and identifies the image information acquired in the non-illuminating state. The identifying information detector 330 determines the imaging unit identifying information and identifies the imaging unit that has acquired the image information.

The image extractor 340 extracts the image information from the image signals input via the synchronization detector 320. The image extractor 340 outputs the extracted image information to the black image compensating unit 380, if the image information is the in-vivo image information acquired in the illuminating state. Meanwhile, the image extractor 340 conducts a processing based on the result of the determination input from the black image determining unit 360 which will be explained later, if the image information is the image information acquired in the non-illuminating state. Specifically, if the image information is the black image, the image extractor 340 outputs the image information to a front black image storage unit 371 or a rear black image storage unit 373, which are constituted by the frame memory and the like. In other words, if the imaging unit that has acquired the image information is the front imaging unit 110-1, the front black image storage unit 371 is rewritten. If the imaging unit that has acquired the image information is the rear imaging unit 110-2, the rear black image storage unit 373 is rewritten.

The black image pixel averaging unit 350 regards the whole area of the image information, which is identified to be acquired in the non-illuminating state by the identifying information detector 330, as determining area, and calculates the average value of the pixel value. For example, in the same manner as the first embodiment, the black image pixel averaging unit 350 integrates each of the pixel value, divides the result of the integration by the number of pixels, and calculates the simple average value of each pixel. The calculated average value is output to the black image determining unit 360.

The black image determining unit 360 compares the average value input from the black image pixel averaging unit 350 with the black image standard value that is predetermined as the threshold value, as a result of the comparison, if the input average value is equal to the black image standard value or less, the black image determining unit 360 determines the image information is the black image. The result of the determination is output to the image extractor 340 via the control unit 410.

The black image compensating unit 380 conducts the image compensation by eliminating the fixed pattern noises in the in-vivo image information based on the black image information. Specifically, the black image compensating unit 380 subtracts the black image information stored in the front black image storage unit 371 from the in-vivo image information, if the in-vivo image information is acquired with the front imaging unit 110-1. In the above mentioned manner, the black image compensating unit 380 eliminates the fixed pattern noises in the in-vivo image information. Meanwhile, if the in-vivo image information is acquired with the rear imaging unit 110-2, the black image compensating unit 380 eliminates the fixed pattern noises in the in-vivo image information by subtracting the black image information stored in the front black image storage unit 373 from the in-vivo image information.

The signal processing unit 390 processes the in-vivo image information compensated with the black image compensating unit 380 to the image data of a desired format, and outputs the image data to a read/write unit 400.

The portable recording medium 50 is detachably attached to the read/write unit 400. The read/write unit 400 sequentially stores the in-vivo image information processed with the signal processing unit 390 in the portable recording medium 50. The read/write unit 400 is realized by the read/write unit that corresponds to the type of the portable recording medium 50.

In the receiving apparatus 30e, configured in the aforementioned manner, the image extractor 340 extracts the image information from the image signal, which is received with one of any receiving antennas A1 to An and demodulated in the receiving unit 310. The image extractor 340 outputs the image information to the black image compensating unit 380, if the image information is the in-vivo image information acquired in the illuminating state. The identifying information detector 330 identifies the image information acquired in the non-illuminating state. The black image pixel averaging unit 350 calculates the average value of the pixel value of the image information which is identified as acquired in the non-illuminating state, and the black image determining unit 360 determines whether the image information is the black image or not. The image information which is determined as the black image is stored, as the black image information, in either the front black image storage unit 371 or the rear black image storage unit 373 depending on the imaging unit that has acquired the black image. The black image compensating unit 380 eliminates the fixed pattern noises in the in-vivo image taken with the front imaging unit 110-1 among the in-vivo image information acquired in the illuminating state, based on the black image information stored in the front black image storage unit 371, and conducts the image compensation. The black image compensating unit 380 eliminates the fixed pattern noises in the in-vivo image taken with the rear imaging unit 110-2 among the in-vivo image information acquired in the illuminating state, based on the black image information stored in the rear black image storage unit 373, and conducts the image compensation. The compensated in-vivo image information is sequentially stored in the portable recording medium 50 with the read/write unit 400.

The in-vivo image information stored in the portable recording medium 50 is read in the displaying apparatus 70 and the image is displayed on the displaying apparatus 70.

According to the third embodiment explained above, the receiving apparatus 30e can determine whether the image information is the black image or not, by calculating the average value of the pixel value of the image information acquired in the non-illuminating state with the capsule endoscope 10e. Therefore the receiving apparatus 30e can securely obtain the black image which is necessary for eliminating the fixed pattern noises in the in-vivo image information. The receiving apparatus 30e can appropriately eliminate the fixed pattern noises in the in-vivo image information acquired in the illuminating state with the capsule endoscope 10e and conduct appropriate image compensation toward the in-vivo image information.

A fourth embodiment will be explained next. The fourth embodiment is an embodiment in which the processes related to the black image determination is conducted with the receiving apparatus. The same referential marks are put to the similar configuration as the third embodiment.

Figure 9:
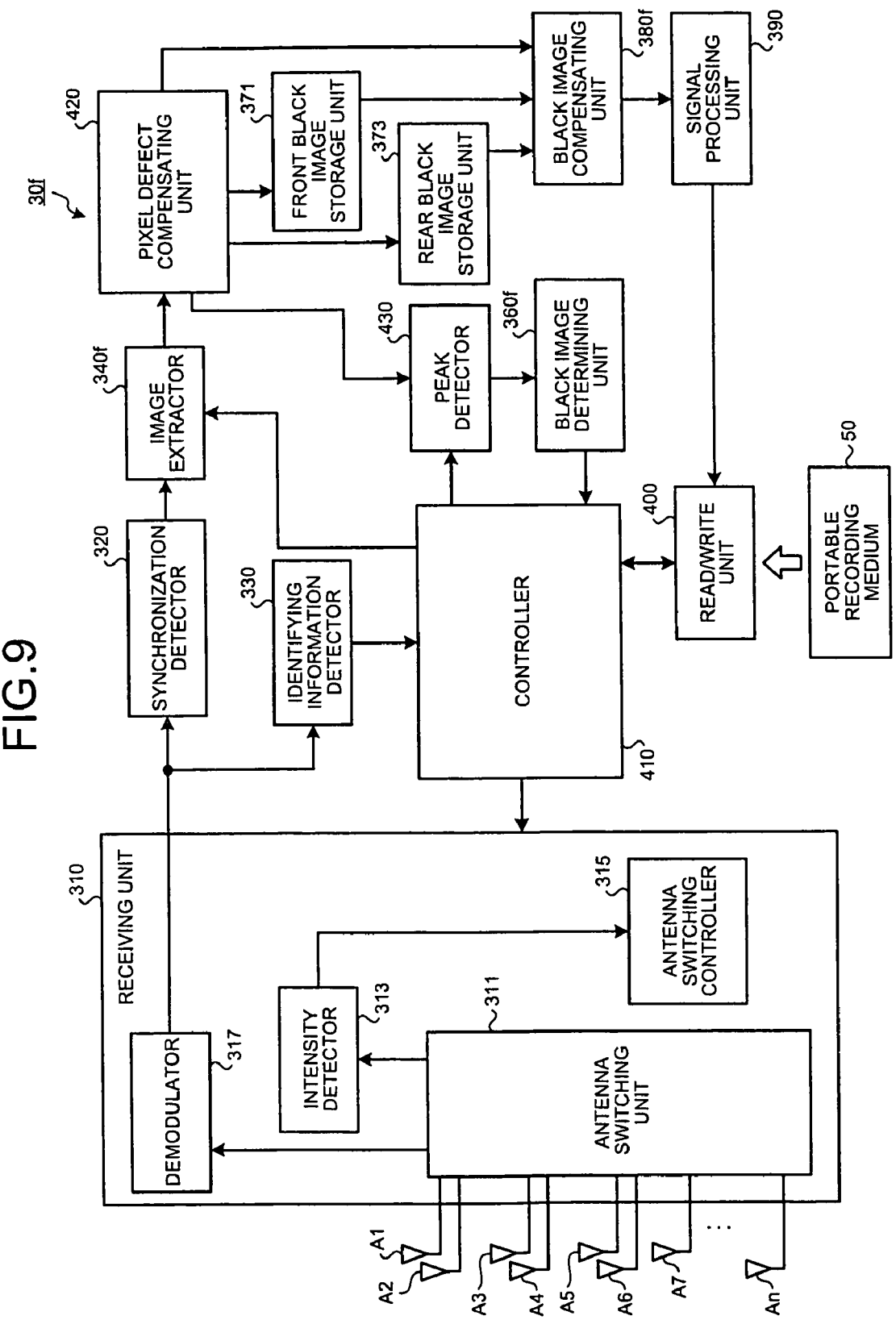
FIG. 9 is a functional block diagram of a receiving apparatus according to a fourth embodiment.

FIG. 9 is a functional block diagram of a receiving apparatus 30f according to the fourth embodiment. The receiving apparatus 30f receives the transmitting signals generated from the capsule endoscope 10e configured as illustrated in FIG. 7. As illustrated in FIG. 9, the receiving apparatus 30f includes, the receiving apparatus 310, the synchronization detector 320, the identifying information detector 330, an image extractor 340f, a pixel defect compensating unit 420, a peak detector 430, a black image determining unit 360f, a black image compensating unit 380f, the signal processing unit 390, the read/write unit 400, and the control unit 410.

The pixel defect compensating unit 420 detects the pixel defects of the image information extracted with the image extractor 340f, and compensates the pixels having the pixel defects. The compensated image information is output to the peak detector 430 and the black image compensating unit 380f.

The peak detector 430 regards, the whole area that is identified as acquired in the non-illuminating state by the identifying information detector 330, as the determining area, and detects the peak value of the pixel value of each pixel that constitutes image information. The detected peak value is output to the black image determining unit 360f.

The black image determining unit 360f compares the peak value input from the peak detector 430 with a black image standard peak value which is predetermined as a threshold value, and as a result of the comparison, if the input peak value is equal to the black image standard peak value or less, the black image determining unit 360f determines the image information is the black image. The result of the determination is output to the image extractor 340f via the control unit 410.

In the receiving apparatus 30f, configured in the aforementioned manner, the image extractor 340f extracts the image information from the image signal, which is received with one of any receiving antennas A1 to An and demodulated in the receiving unit 310. The image extractor 340f outputs the image information to the black image compensating unit 380f, if the image information is the in-vivo image information acquired in the illuminating state. The identifying information detector 330 identifies the image information acquired in the non-illuminating state. The peak detector 430 detects the peak value of the pixel value of each pixel that constitutes the image information identified as acquired in the non-illuminating state, and the black image determining unit 360f determines whether the image information is the black image information or not. The image information determined here, as the black image, is stored as the black image information in either the front black image storage unit 371 or the rear black image storage unit 373, depending on the imaging unit that has acquired the black image.

The black image compensating unit 380f eliminates the fixed pattern noises in the in-vivo image taken with the front imaging unit 110-1, among the in-vivo image information acquired in the illuminating state, based on the black image information stored in the front black image storage unit 371, and conducts the image compensation. The black image compensating unit 380f eliminates the fixed pattern noises in the in-vivo image taken with the rear imaging unit 110-2 among the in-vivo image information acquired in the illuminating state, based on the black image information stored in the rear black image storage unit 373, and conducts the image compensation. The compensated in-vivo image information is sequentially stored in the portable recording medium 50 with the read/write unit 400.

The in-vivo image information stored in the portable recording medium 50 is read in the displaying apparatus 70 and the image is displayed on the displaying apparatus 70.

According to the fourth embodiment explained above, the receiving apparatus 30f can determine whether the image information is the black image or not, by calculating the average value of the pixel value of the image information acquired in the non-illuminating state with the capsule endoscope 10e. Therefore the receiving apparatus 30f can securely obtain the black image which is necessary for eliminating the fixed pattern noises in the in-vivo image information. The receiving apparatus 30f can appropriately eliminate the fixed pattern noises in the in-vivo image information acquired in the illuminating state with the capsule endoscope 10e and conduct appropriate image compensation toward the in-vivo image information.

A fifth embodiment will be explained next. The fifth embodiment is an embodiment, in which the processes related to the determination of the black image and the image compensation, which depends on the result of the determination is conducted with the displaying apparatus.

According to the fifth embodiment, the capsule endoscope is configured in the same manner as the capsule endoscope 10e as explained by illustrating in FIG. 7 in the third embodiment; capsule endoscope 10e is capable of acquiring the in-vivo image information of both the front and rear with respect to the travelling direction of the capsule endoscope 10e. The receiving apparatus receives, from the capsule endoscope, the image information which is transmitted by radio together with the imaging unit identifying information, the illuminating state identifying information, and the adding information, and the receiving apparatus sequentially stores the image information in the portable recording medium 50.

Figure 10:
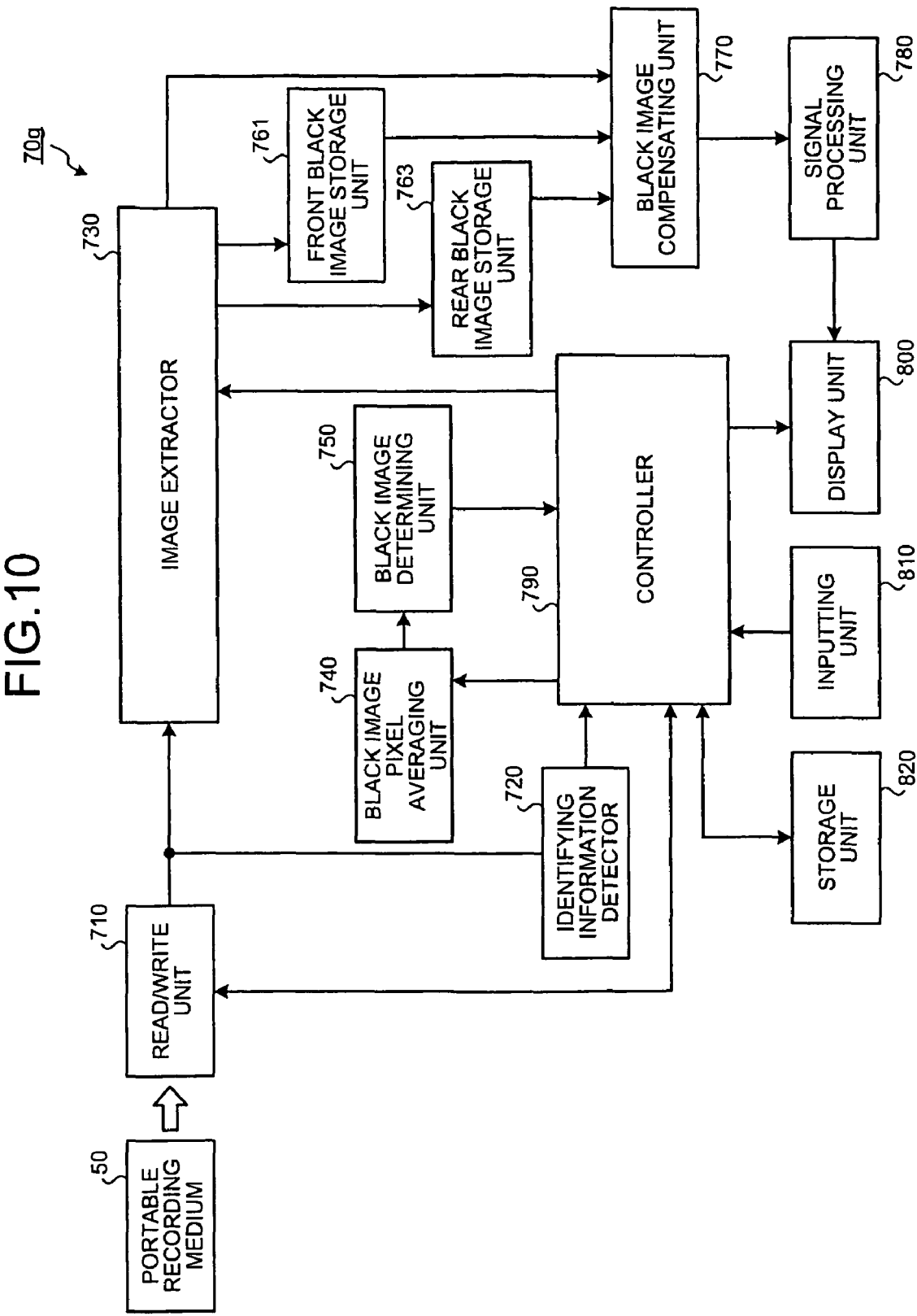
FIG. 10 is a functional block diagram of a displaying apparatus according to a fifth embodiment.

FIG. 10 is a functional block diagram of a displaying apparatus 70g according to the fifth embodiment. The same referential marks are put to the similar configuration as the third embodiment. As illustrated in FIG. 10, the displaying apparatus 70g includes, a read/write unit 710, an identifying information detector 720, an image extractor 730, a black image pixel value averaging unit 740, a black image determining unit 750, a black image compensating unit 770, a signal processing unit 780, a control unit 790, a displaying unit 800, an inputting unit 810, and a storage unit 820. The read/write unit 710 writes data into the portable recording medium 50. The control unit 790 controls the overall operations of the displaying apparatus 70g as a whole.

The displaying unit 800 displays the image of the in-vivo image acquired by the capsule endoscope 10e. The inputting unit 810 is a unit, for conducting a designating operation to designate the in-vivo image to be displayed on the displaying unit 800, and for conducting an inputting operation to input the information concerning the subject 1. The storage unit 820 stores various kinds of data needed for the operation of the displaying apparatus 70g.

Figure 11:
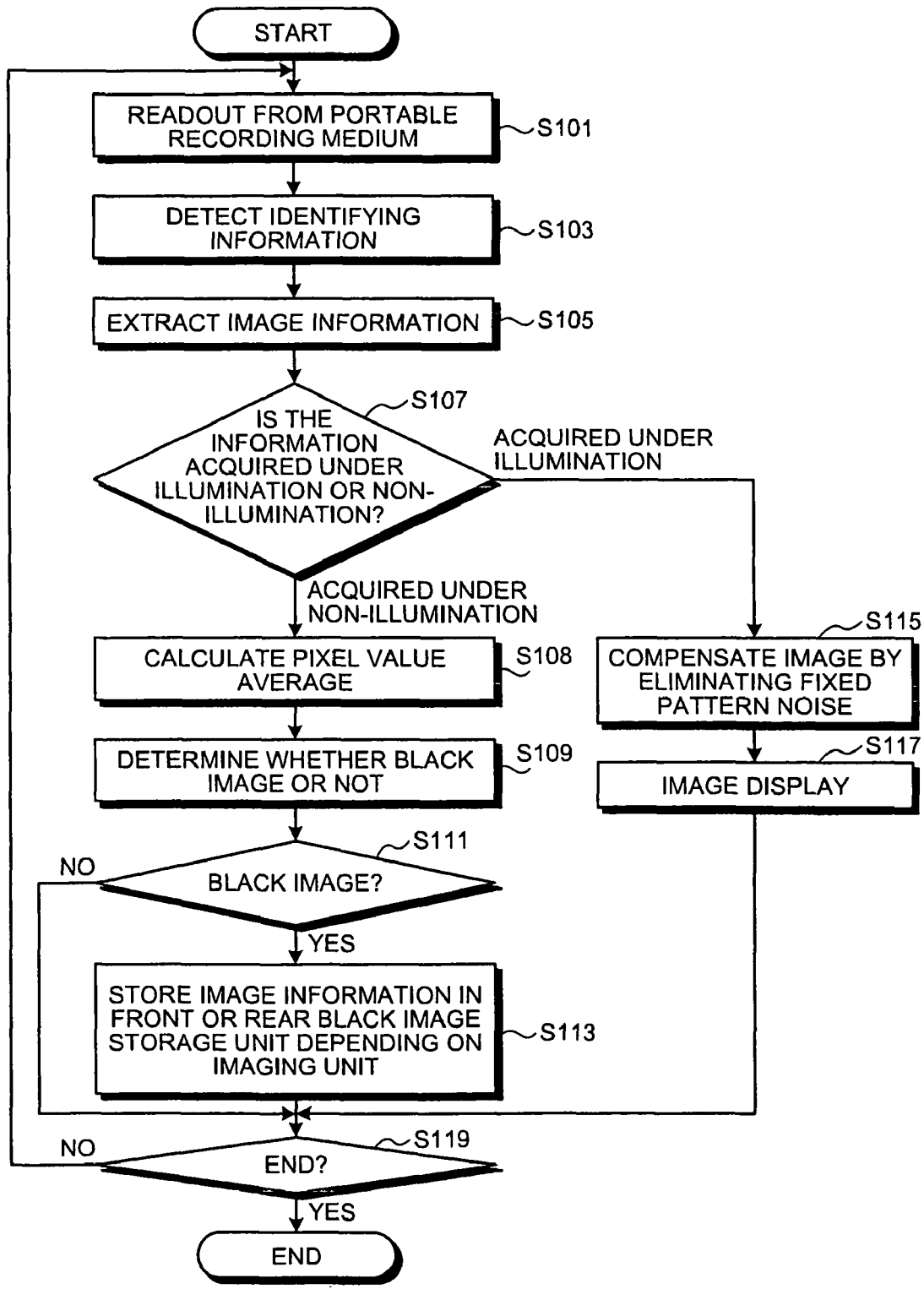
FIG. 11 is a flowchart showing a flow of operations of the displaying apparatus according to the fifth embodiment.

FIG. 11 is a flowchart showing a flow of operations of the displaying apparatus 70g according to the fifth embodiment. As illustrated in FIG. 11, first, the read/write unit 710 reads out, from the portable recording medium 50 which is attached to the read/write unit 710, the image information that is stored together with the imaging unit identifying information, the illuminating state identifying information, and the adding information (step S101). Subsequently, the identifying information detector 720 detects the imaging unit identifying information, and the illuminating state identifying information (step S103). By these steps, the imaging unit that has acquired the read out image information is identified, and whether the read out image information is the image information acquired in the non-illuminating state or in the illuminating state is identified. The image extractor 730 extracts the image information (step S105). If the extracted image information is the in-vivo image information acquired in the illuminating state, the extracted image information is output to the black image compensating unit 770.

Subsequently, the illuminating state identifying information detected in the step S105 is examined (step S107), the displaying apparatus 70g conducts the operation which depends on whether the image information is taken in the illuminating state or non-illuminating state. Specifically, in the case of the image information acquired in the non-illuminating state, first, the black image pixel value averaging unit 740 calculates the average value of the pixel value of the image information (step S108). For example, the black image pixel value averaging unit 740 regards the whole area of the acquired image information as the determining area, integrates the pixel value of each pixel that constitutes the image information, divides the result of the integration by the number of pixels, and calculates the simple average value of each pixel. Subsequently, the black image determining unit 750 determines whether the image information is the black image or not (step S109). If the image information is determined to be the black image (step S111: Yes), the image information is, depending on the imaging unit that has acquire the image information, output to the front imaging unit 110-1 or stored in a rear black image storage unit 763 (step S113). Specifically, if the imaging unit that has acquired the image information is the front imaging unit 110-1, the image information is output to a front black image storing unit 761 and stored there, and if the imaging unit that has acquired the image information is the rear imaging unit 110-2, the image information is output to the rear black image storage unit 763 and stored there.

Meanwhile, in the case of the in-vivo image information, which is identified to be acquired in the illuminating state, the black image compensating unit 770 eliminates the fixed pattern noises in the in-vivo image information based on the black image information, and conducts the image compensation (step S115). Specifically, if the in-vivo image information is taken with the front imaging unit 110-1, the black image compensating unit 770 eliminates the fixed pattern noises in the in-vivo image information based on the black image information stored in the front black image storing unit

761, and conducts the image compensation. If the in-vivo image information is taken with the rear imaging unit 110-2, the black image compensating unit 770 eliminates the fixed pattern noises in the in-vivo image information based on the black image information stored in the rear black image storing unit 763, and conducts the image compensation. The displaying unit 800 displays the compensated in-vivo image information (step S117). The displaying apparatus 70g repeats the aforementioned steps by returning to step 101 until the image display ends (step S119: No), and sequentially reads out the information stored in the portable recording medium 50 and displays the image on the displaying unit 800.

According to the fifth embodiment explained above, the displaying apparatus 70g can determine whether the image information is the black image or not, by calculating the average value of the pixel value of the image information, acquired in the non-illuminating state with the capsule endoscope 10. Therefore the displaying apparatus 70g can securely obtain the black image which is necessary for eliminating the fixed pattern noises in the in-vivo image information. The displaying apparatus 70g can appropriately eliminate the fixed pattern noises in the in-vivo image information acquired in the illuminating state with the capsule endoscope 10 and conduct appropriate image compensation toward the in-vivo image information.

A sixth embodiment will be explained next. The sixth embodiment is an embodiment, in which the processes related to the determination of the black image and the image compensation are conducted with the displaying apparatus. The same referential marks are put to the similar configuration as the fifth embodiment.

Figure 12:
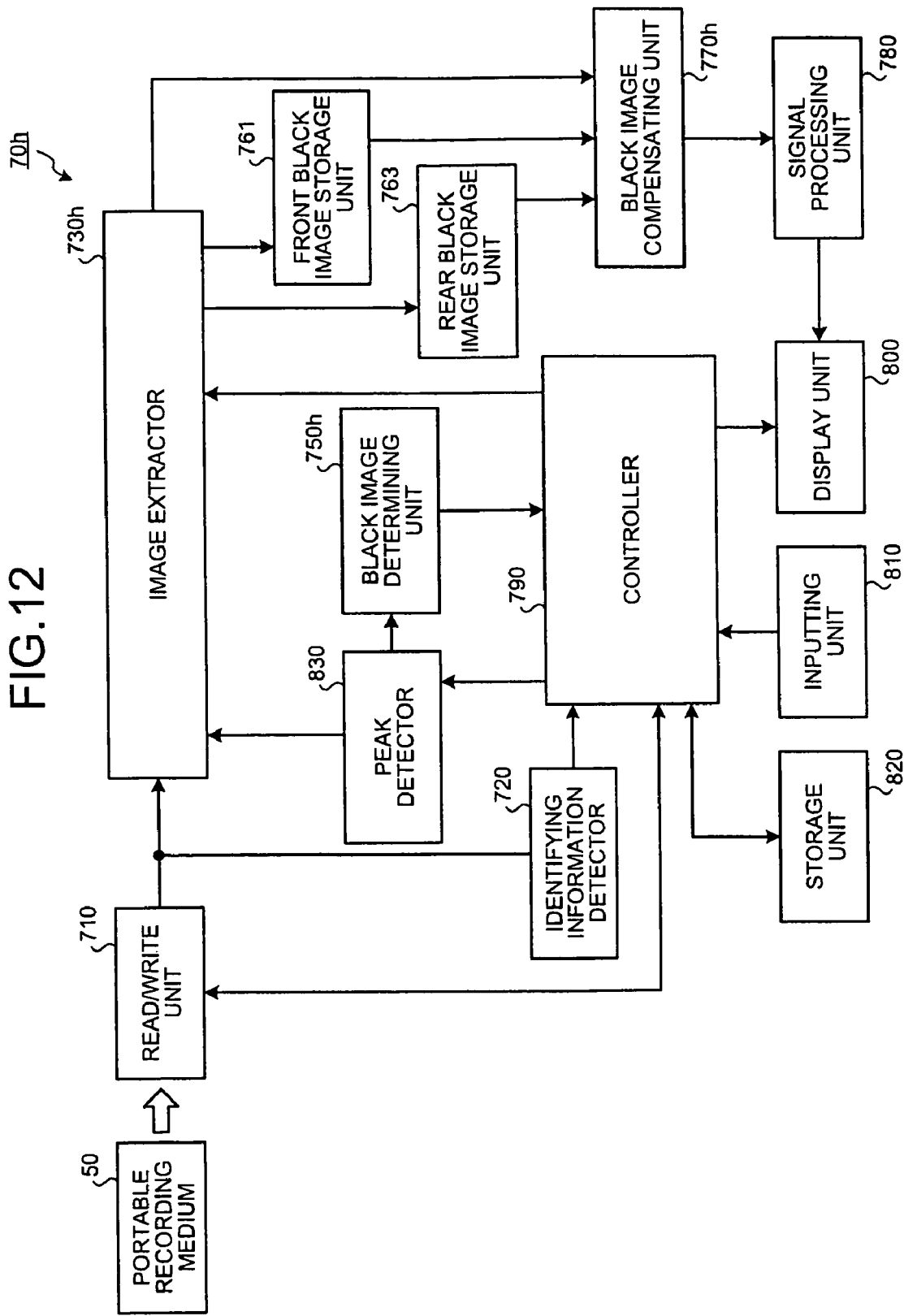
FIG. 12 is a functional block diagram of a displaying apparatus according to a sixth embodiment.

FIG. 12 is a functional block diagram of a displaying apparatus 70h according to the sixth embodiment. As illustrated in FIG. 12, the displaying apparatus 70h includes, the read/write unit 710, an image extractor 730h, the identifying information detector 720, a peak detector 830, a black image determining unit 750h, a black image compensating unit 770h, a signal processing unit 780, the control unit 790, the inputting unit 810, the displaying unit 800, and the storage unit 820. The read/write unit 710 conducts read/write of the data to the portable recording medium 50.

In the displaying apparatus 70h which is configured in the aforementioned manner, first, the read/write unit 710 reads out, from the portable recording medium 50, the image information stored together with the imaging unit identifying information, the illuminating state identifying information, and the adding information. Subsequently, the identifying information detector 720 detects the imaging unit identifying information, and the illuminating state identifying information, and the image extractor 730h extracts the image information.

Subsequently, if the image information is the image information acquired in the non-illuminating state, the peak detector 830 detects the peak value of the pixel value of the image information, and the black image determining unit 750h determines whether the image information is the black image or not. The image information that is determined to be the black image here is stored in either the front black image storing unit 761 or the rear black image storage unit 763. Meanwhile, if the image information is the in-vivo image information acquired in the illuminating state, the black image compensating unit 770h eliminates the fixed pattern noises in the in-vivo image information based on the black image information, and conducts the image compensation. The displaying unit 800 displays the image of the compensated in-vivo image information. The displaying apparatus 70h sequentially reads out the image information stored in the portable recording medium 50 by repeating the aforementioned operations, and displays the image on the displaying unit 800.

In the sixth embodiment, the peak value of the image information extracted with the image extractor 730h is directly detected. Alternatively, it is possible to compare the pixel value of the notable pixel with pixel values of pixels around the notable pixel, in the image information detected with the image extractor 730h. If the pixel value of the notable pixel is largely different from that of the pixels around the notable pixel, the notable pixel is regarded as defective, and it is possible to conduct the peak value detection toward the image that is given a pixel defect compensating processing. In this case, a pixel defect compensation unit that conducts the pixel defect compensating processing is provided to the displaying apparatus 70h. The pixel defect compensating unit detects the pixel defect in the image information that is extracted with the image extractor 730h, compensates the pixels that have the pixel defect in the image information, and outputs the image information to the peak detector 830. The peak detector 830 detects the peak value of the pixel value of each pixel targeting the image information of which pixel defects are compensated with the pixel defect compensating unit. If a pixel having a large value such as white spot is included in the image, the pixel is compensated with the pixel defect compensating processing; therefore even the image that contains the white spot can be precisely recognized as the black image.

According to the above explained sixth embodiment, the displaying apparatus 70h can determine whether the image information is the black image or not by calculating the peak value of the pixel value of each pixel that constitutes the image information that is acquired in the illuminating state in the capsule endoscope. Therefore the displaying apparatus 70h can securely obtain the black image that is necessary for eliminating the fixed pattern noises in the in-vivo image information. Then, the displaying apparatus 70h can eliminate the fixed pattern noises in the in-vivo image information that is acquired in the illuminating state in the capsule endoscope, and can conduct appropriate image compensation toward the in-vivo image information.

Although, in the aforementioned first, third, and fifth embodiments, to determine whether the image information acquired in the non-illuminating state with the capsule endoscope, the black image pixel averaging unit calculates the simple average value of the pixel value of each pixel that constitutes image information, the embodiments are not limited to the above mentioned method.

For example, the weighted average value of the RGB value of each pixel that constitutes the image information may be calculated. In this case, the standard luminance value is predetermined as the threshold value; the black image determining unit determines whether the image information is the black image or not, by comparing the calculated weighted average value with the black image standard luminance value. Alternatively, the average value of predetermined color component of each pixel that constitutes the image information may be calculated. In this case, any one of RGB may be adopted as the color component to calculate the average value. In this case, the standard color component value is predetermined as the threshold value, the black image determining unit determines whether the image information is the black image or not by comparing the calculated average value with the standard color component value.

In the aforementioned first, third, and fifth embodiments, to determine whether the image information acquired in the non-illuminating state with the capsule endoscope, the black image pixel averaging unit is made to calculate the average value of the pixel value by regarding the whole area of the image information as the determining area. Alternatively, the determining area may be predetermined, and out of the targeted image information, the average value of the pixel value included in the predetermined determining area may be calculated.

In the aforementioned second, fourth, and sixth embodiments, to determine whether the image information acquired in the non-illuminating state with the capsule endoscope, the peak detector is made to detect the peak value of the pixel value of each pixel regarding the whole area of the image information as the determining area. Alternatively, the determining area may be predetermined, and out of the targeted image information, the peak value of the pixel value of each pixel that constitutes determining area may be detected.

Although, in the first and second embodiments, the image information is acquired in the non-illuminating state by conducting the black image acquiring operation at a predetermined time interval (10 minutes), the timing of acquiring the black image acquiring operation is not limited to this.

Figure 13:
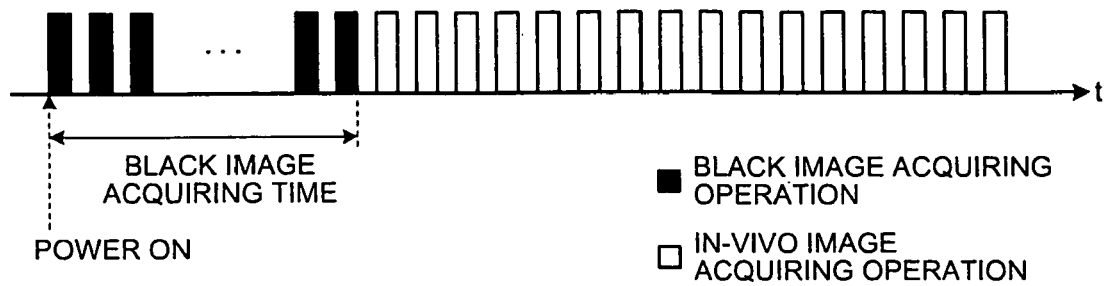
FIG. 13 is an exemplary variation of timings of the in-vivo image information acquiring operation and black image acquiring operation.

FIG. 13 is an exemplary variation for explaining timings of the in-vivo image information acquiring operation and black image acquiring operation.

In the example illustrated in FIG. 13, the imaging operation by the imaging unit is conducted at a predetermined interval (0.5 second) in the same manner as the aforementioned first and second embodiments. After the power source to the capsule endoscope is turned on, until a predetermined time passes the black image acquiring operation is conducted. In this case a timer is provided to the capsule endoscope. The timer, for example, starts up when the power is turned on, and counts the elapse time until the black image acquiring time elapses, by counting the elapse time from the start up.

Figure 14:
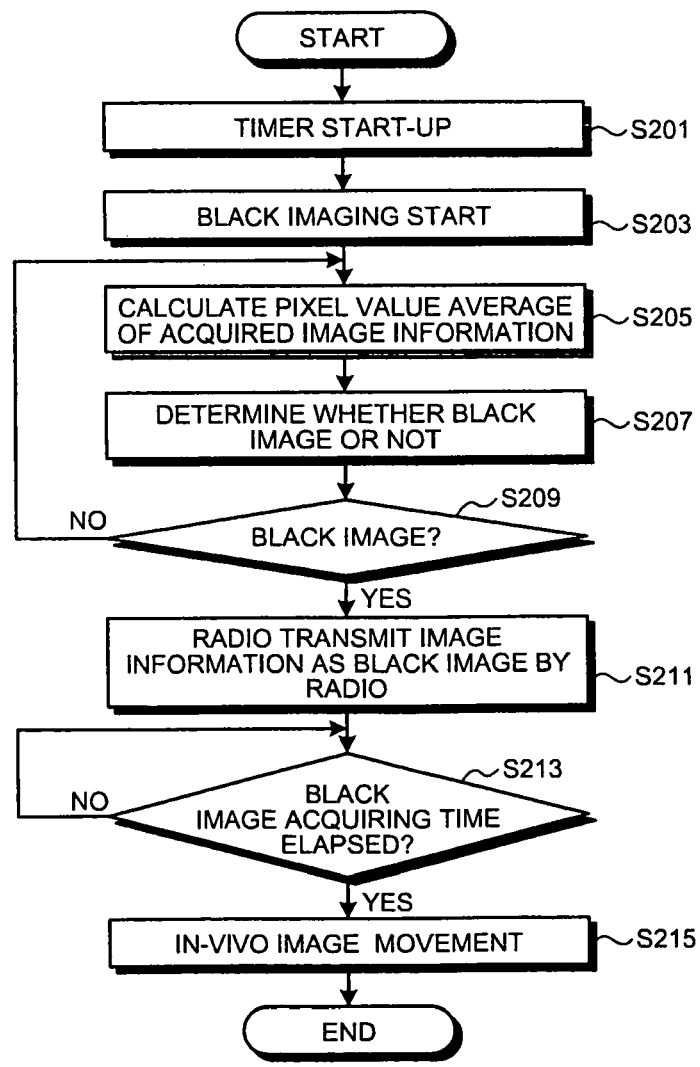
FIG. 14 is a flowchart showing a flow of operations of the capsule endoscope according to an exemplary variation.

FIG. 14 is a flowchart showing a flow of operations of the capsule endoscope according to an exemplary variation. As illustrated in FIG. 14, according to the present exemplary variation, upon the power is turned on, at first the timer is activated and the timer starts counting the black image acquiring time (step S203). The capsule endoscope calculates the average value of the pixel value of the image information, acquired in the non-illuminating state, by the started black image acquiring operation (step S205), and determines whether the image information is the black image or not by comparing the calculated average value with the predetermined standard average value (step S207). If the image information is determined not to be the black image (step S209: No), the aforementioned operation is repeated by returning to the step S205. Meanwhile, if the image information is determined to be the black image (step S209: Yes), the image information is transmitted to outside the body by radio (step S211). When the lapse time counted by the timer reaches the black image acquiring time (step S213: Yes), the capsule endoscope starts the in-vivo image acquiring operation (step S215). The present operation is an operation on the assumption that the capsule endoscope is taken into the body of the subject 1 immediately after the power is turned on, the image information of the black image can be acquired and transmitted to the receiving apparatus 30 prior to the start of the in-vivo image acquiring operation.

Figure 15:
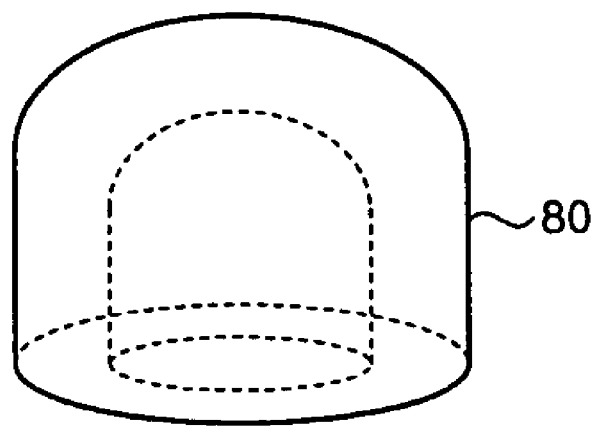
FIG. 15 is a schematic view of a cap which detachably covers the capsule endoscope according to an exemplary variation.
Figure 16:
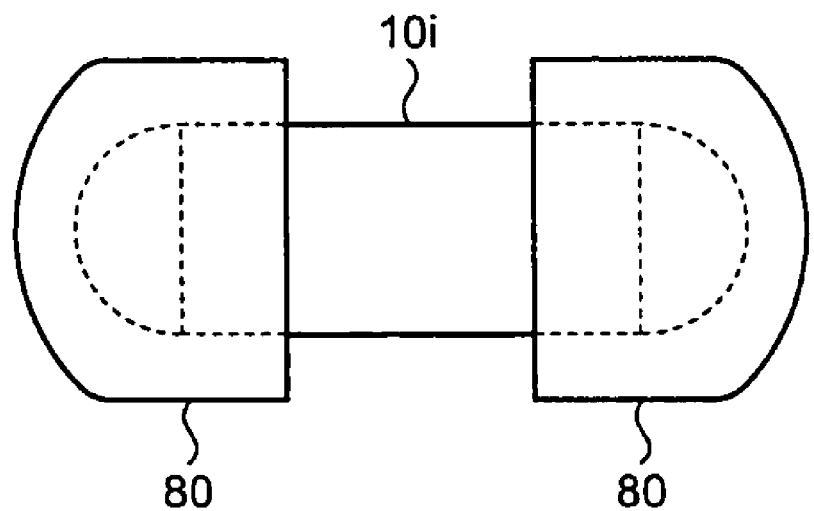
FIG. 16 is a schematic view of the caps when the caps are attached to the capsule endoscope.

Alternatively, the image information may be acquired in the non-illuminating state by conducting a predetermined times of the black image acquiring operations (for example 20 times) after the power of the capsule endoscope is turned on. Alternatively, the black image may be acquired in a state the caps are attached to the optical windows of the capsule endoscope. FIG. 15 is a schematic view of a cap 80. FIG. 16 is a schematic view when the caps 80 illustrated in FIG. 15 are attached to the capsule endoscope 10i. The capsule endoscope 10i is configured in the same manner as the capsule endoscope 10e illustrated in FIG. 7 in the third embodiment. The capsule endoscope 10i is capable of acquiring the in-vivo image information of both the front and rear image information with respect to the travelling direction of the capsule endoscope 10i, and the top covers that function as the optical windows at both ends of the capsule endoscope 10i are covered and light shielded with the caps 80.

In this case, for example, the black image may be acquired by conducting the black image acquiring operation in the non-illuminating state, during the time after the power of the capsule endoscope is turned on until a predetermined time elapses. Alternatively, the black image may be acquired by conducting the black image acquiring operations for predetermined times in the non-illuminating state, after the power of the capsule endoscope is turned on.

Alternatively, the capsule endoscope may be configured to detect the removal of the caps 80, upon detection of the removal of the caps 80 the in-vivo image acquiring operation may be started. In this case, the capsule endoscope 10 is provided with a function that determines whether the caps 80 are removed or not. For example, the capsule endoscope determines whether the caps 80 are removed or not by determining the brightness of the image information based on the average value calculated by the black image pixel value averaging unit 137 according to the first embodiment. Specifically, the threshold value (standard average value) that determines whether the image information is the black image, and another threshold value that determines whether the caps 80 are removed are predetermined. The black image determining unit determines whether the acquired image information is the black image or not by comparing the aforementioned threshold values with the calculated average value, and determines whether the caps 80 are removed. Alternatively, the black image determining unit determines whether the caps 80 are removed by determining the brightness of the acquired image information based on the average value calculated by the peak detector 147 according to the second embodiment.

FIG. 17 is a flowchart showing a flow of operations of the capsule endoscope according to an exemplary variation. As illustrated in FIG. 17, the capsule endoscope of the exemplary variation starts the black image acquiring operation upon the power is turned on (step S301). The capsule endoscope calculates the average value of the pixel value of the image information, acquired in the non-illuminating state by the started black image acquiring operation, and determines whether the image information is the black image or not based on the calculated average value (step S303). If the image information is determined not to be the black image (step S305: No), returns to step S303 and repeats the aforementioned operations. In the meantime, if the image information is determined to be the black image (step 305: Yes), the capsule endoscope transmits the image information to outside the body by radio (step S307).

In step S307, after transmitting the image information of the black image by radio, the capsule endoscope calculates the average value of the pixel value of the image information that is sequentially acquired in the non-illuminating state, and determines whether the caps 80 are removed based on the calculated average value (step S308). In this case, whether the caps 80 are removed or not may be determined, on condition that the image information of which calculated average value is equal to or over the threshold value, which is used to determine whether the caps 80 are removed or not are acquired continuously for several times. If it is determined the caps 80 are not removed (step S309: No), aforementioned operation is repeated by returning to step 308, meanwhile if the capsule endoscope determines the caps 80 are removed (step S309: Yes), the capsule endoscope starts the in-vivo image acquiring operation (step S311). According to the present exemplary variation, it is possible to previously acquire, during the time between the power is turned on and the caps 80 are removed, the image information of the black image and transmit it to the receiving apparatus 30.

The in-vivo image acquiring apparatus, in-vivo image receiving apparatus, in-vivo image displaying apparatus, and noise eliminating method of the present embodiments can calculate the average value of the pixel value of the image information acquired in the non-illuminating state. According to the present embodiments it is possible to determine whether the image information is the black image or not by comparing the acquired average value with the predetermined threshold value. Alternatively, it is possible to determine whether the image information is the black image or not, by detecting the peak value of the pixel value of each pixel that constitutes the image information acquired in the non-illuminating state, and by comparing the acquired peak value with the predetermined threshold value. Therefore it is possible to securely acquire the black image which is necessary to eliminate the fixed pattern noises in the in-vivo image information. According to the embodiments, based on the image information determined to be the black image, it is possible to appropriately eliminate the fixed pattern noises in the image information acquired in the illuminating state, and conduct appropriate image compensation toward the image information.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An in-vivo image acquiring apparatus to be taken into a body of a subject, comprising:
an imaging unit that acquires in-vivo image information;
an illuminating unit that illuminates imaging regions of which images are taken by the imaging unit;
a radio transmitting unit that transmits the image information acquired by the imaging unit to an external apparatus by radio;
an operation control unit that controls operations of the imaging unit and the illuminating unit so as to control a black image acquiring operation in which the imaging unit conducts an imaging operation with the illuminating unit not conducting an illuminating operation;
an average value calculating unit that calculates an average value of pixel values of a predetermined determining area among the image information acquired by the black image acquiring operation;
a black image determining unit that determines whether the image information acquired by the black image acquiring operation indicates a black image by comparing the average value calculated by the average value calculating unit with a predetermined threshold value; and
a dimmer controller that controls an amount of illuminating light emitted by the illuminating unit depending on a brightness of a predetermined dimming area based on the image information acquired by the imaging unit, wherein
the radio transmitting unit transmits to the external apparatus by radio the image information which is determined by the black image determining unit as the black image, as black image information, and
the average value calculating unit calculates the average value of pixel values which are included in the dimming area by regarding the dimming area as the determining area.

2. The in-vivo image acquiring apparatus according to claim 1, wherein
the average value calculating unit calculates a simple average value of pixel values of pixels that constitute the determining area based on the image information acquired by the black image acquiring operation.

3. The in-vivo image acquiring apparatus according to claim 1, wherein
the average value calculating unit calculates a weighted average value of RGB values of pixels that constitute the determining area based on the image information acquired by the black image acquiring operation.

4. The in-vivo image acquiring apparatus according to claim 1, wherein
the average value calculating unit calculates an average value of predetermined color components of pixels that constitute the determining area based on the image information acquired by the black image acquiring operation.

5. An in-vivo image receiving apparatus for receiving in-vivo image information from an in-vivo image acquiring apparatus which is taken into a body of a subject and which acquires the in-vivo image information in an illuminating state or in a non-illuminating state, the in-vivo image receiving apparatus comprising:
an average value calculating unit that calculates an average value of pixel values of a predetermined determining area among the image information acquired in the non-illuminating state by the in-vivo image acquiring apparatus;
a black image determining unit that determines whether the image information acquired in the non-illuminating state by the in-vivo image acquiring apparatus indicates a black image by comparing the average value calculated by the average value calculating unit with a predetermined threshold value;
a black image storage unit that stores as black image information the image information determined as the black image by the black image determining unit;
a black image compensating unit that, based on the black image information stored in the black image storage unit, eliminates fixed pattern noises in the image information acquired in the illuminating state by the in-vivo image acquiring apparatus, and compensates the image information; and
a dimmer controller that controls an amount of illuminating light emitted by the in-vivo image acquiring apparatus depending on a brightness of a predetermined dimming area based on the image information acquired by the in-vivo image acquiring apparatus, wherein
the average value calculating unit calculates the average value of pixel values which are included in the dimming area by regarding the dimming area as the determining area.

6. The in-vivo image receiving apparatus according to claim 5, wherein
the average value calculating unit calculates a simple average value of pixel values of pixels that constitute the determining area based on the image information acquired in the non-illuminating state.

7. The in-vivo image receiving apparatus according to claim 5, wherein
the average value calculating unit calculates a weighted average value of RGB values of pixels that constitute the determining area based on the image information acquired in the non-illuminating state.

8. The in-vivo image receiving apparatus according to claim 5, wherein
the average value calculating unit calculates an average value of predetermined color components of pixels that constitute the determining area based on the image information acquired in the non-illuminating state.

9. An in-vivo image displaying apparatus for displaying image information acquired by an in-vivo image acquiring apparatus which is taken into a body of a subject and acquires in-vivo image information in an illuminating state or in a non-illuminating state, the in-vivo image displaying apparatus comprising:
a black image pixel value averaging unit that calculates an average value of pixel values of a predetermined determining area among the image information acquired in a non-illuminating state by the in-vivo image acquiring apparatus;
a black image determining unit that determines whether the image information acquired in the non-illuminating state indicates a black image by comparing the average value calculated by the black image pixel value averaging unit with a predetermined threshold value;
a black image storage unit that stores as black image information the image information determined as the black image by the black image determining unit;
an image compensating unit that, based on the black image information stored in the black image storage unit, eliminates fixed pattern noises in the image information acquired in the illuminating state by the in-vivo image acquiring apparatus, and compensates the image information; and
a dimmer controller that controls an amount of illuminating light emitted by the in-vivo image acquiring apparatus depending on a brightness of a predetermined dimming area based on the image information acquired by the in-vivo image acquiring apparatus, wherein the black image pixel value calculating unit calculates the average value of pixel values which are included in the dimming area by regarding the dimming area as the determining area.

10. The in-vivo image displaying apparatus according to claim 9, wherein
the average value calculating unit calculates a simple average value of pixel values of pixels that constitute the determining area based on the image information acquired in the non-illuminating state.

11. The in-vivo image displaying apparatus according to claim 9, wherein
the average value calculating unit calculates a weighted average value of RGB values of pixels that constitute the determining area based on the image information acquired in the non-illuminating state.

12. The in-vivo image displaying apparatus according to claim 9, wherein
the average value calculating unit calculates an average value of predetermined color components of pixels that constitute the determining area based on the image information acquired in the non-illuminating state.

13. A noise eliminating method for eliminating fixed pattern noises in in-vivo image information, the method comprising:
acquiring the in-vivo image information in a non-illuminating state;
calculating an average value of a predetermined determining area among the image information acquired in the non-illuminating state;
determining whether the image information acquired in the non-illuminating state indicates a black image by comparing the calculated average value with a predetermined threshold value;
acquiring the in-vivo image information in an illuminating state while controlling an amount of illuminating light depending on a brightness of a predetermined dimming area; and
eliminating the fixed pattern noises in the image information acquired in the illuminating state and compensating the image information based on the image information determined as the black image, wherein the dimming area is regarded as the determining area.

* * * * *